United States Patent
Hakansson et al.

(10) Patent No.: US 9,526,766 B2
(45) Date of Patent: Dec. 27, 2016

(54) POTENTIATION OF ANTIBIOTIC TREATMENT WITH A PROTEIN-LIPID COMPLEX

(71) Applicant: The Research Foundation for The State University of New York, Amherst, NY (US)

(72) Inventors: Anders P. Hakansson, East Amherst, NY (US); Laura R. Marks, Buffalo, NY (US); Hazeline Hakansson, East Amherst, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 0 days.

(21) Appl. No.: 14/412,104

(22) PCT Filed: Jul. 5, 2013

(86) PCT No.: PCT/US2013/049437
§ 371 (c)(1),
(2) Date: Dec. 30, 2014

(87) PCT Pub. No.: WO2014/008465
PCT Pub. Date: Jan. 9, 2014

(65) Prior Publication Data
US 2015/0148286 A1    May 28, 2015

Related U.S. Application Data

(60) Provisional application No. 61/668,390, filed on Jul. 5, 2012.

(51) Int. Cl.
*A61K 38/38* (2006.01)
*A61K 31/43* (2006.01)
*A61K 31/7036* (2006.01)
*A61K 31/7048* (2006.01)

(52) U.S. Cl.
CPC .............. *A61K 38/38* (2013.01); *A61K 31/43* (2013.01); *A61K 31/7036* (2013.01); *A61K 31/7048* (2013.01)

(58) Field of Classification Search
CPC .... A61K 38/38; A61K 31/43; A61K 31/7036; A61K 31/7048; A61K 2300/00
See application file for complete search history.

(56) References Cited

U.S. PATENT DOCUMENTS

| | | |
|---|---|---|
| 6,808,930 B1 | 10/2004 | Svanborg et al. |
| 7,053,185 B1 | 5/2006 | Svanborg et al. |
| 7,524,932 B2 | 4/2009 | Svanborg et al. |
| 2010/0029557 A1* | 2/2010 | Sigh .............. A61K 31/20 514/8.9 |

FOREIGN PATENT DOCUMENTS

| | | | |
|---|---|---|---|
| WO | 2011/075691 A1 | 6/2011 | |
| WO | WO2011/075691 | * 6/2011 | |
| WO | WO2011/075691 A1 * | 6/2011 | ............... A61K 9/64 |

OTHER PUBLICATIONS

Antibiotic Potentiation, J. H. Hare, Can. J. Comp. Med. Vet. Sci., vol. 24, Jun. 1960, pp. 171-176.*
Kodner et al., Recurrent Urinary Tract Infections in Women: Diagnosis and Management, Am. Fam. Phys., Sep. 15, 2010, vol. 82, No. 6, 638-643.*
Susan A. Mehnert-Kay, Diagnosis and Management of Uncomplicated Urinary Tract Infections, Am. Fam. Phys., Aug. 1, 2005, vol. 72, No. 3, 451-456.*
Mossberg et al., Bladder cancers respond to intravesical instillation of HAMLET (human a-lactalbumin made lethal to tumor cells), Int. J. Cancer: 121, 1352-1359 (2007).*
Knyazeva et al., Who is Mr. HAMLET? Interaction of Human R-Lactalbumin with Monomeric Oleic Acid, Biochemistry 2008, 47, 13127-13137.*
Swedish Dairy Association, Fatty acids in bovine milk fat, Food & Nutrition Research 2008, pp. 1-3.*
Hakansson et al., Proc. Natl. Acad. Sci. USA 92, 1995, 8064-806.*
Antimicrobial Peptides from Food Proteins Author: Pellegrini, A., Current Pharmaceutical Design, vol. 9, No. 16, Jun. 2003, pp. 1225-1238(14).*
Kamill Gal, Combined Antibiotic Therapy, Canad. Med. Ass. J. vol. 93, pp. 844-847, 1965.*
Mossberg et al., Bladder cancers respond to intravesical instillation of HAMLET (human a-lactalbumin made lethal to tumor cells) Int. J. Cancer:121,1352-1359, 2007.*
Marks, L.R., et al., Sensitization of *Staphylococcus aureus* to Methicillin and Other Antibiotics In Vitro and In Vivo in the Presence of HAMLET, PLOS One, May 2013, vol. 8, No. 5, pp. 1-11.
Marks, L.R., et al., The Human Milk Protein-Lipid Complex HAMLET Sensitizes Bacterial Pathogens to Traditional Antimicrobial Agents, PLOS One, Aug. 2012, vol. 7, No. 8, pp. 1-13.
Brest et al., Histone deacetylase inhibitors promote the tumoricidal effect of HAMLET, Cancer Research, vol. 67, No. 23, pp. 11327-11334. Dec. 1, 2007.
Mossberg et al., Bladder cancers respond to intravesical installation of HAMLET (human alpha-lactalbumin made lethal to tumor celss), International Journal of Cancer, vol. 121, No. 6, pp. 1352-1359. Sep. 15, 2007.

* cited by examiner

Primary Examiner — Lianko Garyu
Assistant Examiner — Joseph Fischer
(74) *Attorney, Agent, or Firm* — Hodgson Russ LLP

(57) ABSTRACT

Provided are compositions and methods for potentiating the effect of antibiotics. The compositions comprise a non-covalent complex of alpha-lactalbumin and fatty acid. The fatty acids are cis, unsaturated, C14 to C20 fatty acids. The complex and antibiotic can be administered to an individual together or separately. The antibiotic may be one to which resistance has developed.

16 Claims, 17 Drawing Sheets

POTENTIATION OF ANTIBIOTIC TREATMENT WITH A PROTEIN-LIPID COMPLEX

CROSS-REFERENCE TO RELATED APPLICATIONS

This application claims priority to U.S. Provisional Application No. 61/668,390, filed on Jul. 5, 2012, the disclosure of which is incorporated herein by reference.

FIELD OF THE DISCLOSURE

This disclosure relates generally to the field of treatment of infectious diseases, and more particularly to compositions and methods to potentiate the activity of antibiotics.

BACKGROUND OF THE DISCLOSURE

Emergence of antibiotic resistance is a major health care concern. Since the discovery of penicillin, at least 17 different classes of antibiotics have been produced. Antibiotic use has become widespread and a cornerstone of medical treatment—being used to treat infections ranging from the seriously life-threatening to the more trivial and frequently non-bacterial illnesses. This constant antibiotic pressure, combined with the ability of bacteria to incorporate DNA from other strains and closely related species, has led to the evolution and acquisition of resistance traits. Multiple-antibiotic-resistant strains are now widespread and bacteria have developed at least one mechanism of resistance (and frequently many more) to every single antibiotic class. For example, Methicillin-resistant *Staphylococcus aureus* (MRSA) is one of the principal multi-drug resistant bacterial pathogens causing serious community and hospital-acquired infections, such as skin and soft tissue infections, bone, joint and implant infections, ventilator-associated pneumonia, and sepsis. It is estimated that multi-drug resistant *Staphylococcus aureus* infections leads to 19,000 deaths per year in the United States, with an associated 3-4 billion US dollars in additional annual health care costs. Despite this high mortality rate, there are relatively few new antibacterial agents in the pharmaceutical pipeline. Instead, the majority of antibiotics developed in the last decade are molecules re-engineered from existing antibiotic classes for which underlying resistance mechanisms are already present. Therefore effective new therapeutic options for treatment of infections caused, particularly those caused by multi-drug resistant bacteria are urgently needed.

BRIEF SUMMARY OF THE DISCLOSURE

This disclosure is based on the unexpected observation that a non-covalent complex of alpha-lactalbumin and fatty acid (α-lactalbumin fatty acid complex, hereinafter, "ALAFAC") potentiates the activity of antibiotics. In one aspect, the present disclosure provides compositions for use in inhibiting the growth of bacteria. In one embodiment, the composition comprises α-lactalbumin fatty acid complex and one or more antibiotics. In one embodiment, the composition comprises ALAFAC without the antibiotic in an amount that is sufficient to act as an adjuvant to the activity of an antibiotic but is not sufficient to have a detectable bactericidal activity by itself.

In one aspect, this disclosure provides a method of reducing the growth of bacteria comprising the step of contacting the bacteria with ALAFAC and an antibiotic. The bacteria may be contacted with the ALAFAC and an antibiotic, together or separately. The bacteria may be residing in a mammalian body (such as a human body), on a mammalian body, or may be at a site outside the body.

In one aspect, this disclosure provides kits for treatment of bacterial infections. The kit comprises compositions comprising ALAFAC with or without one or more antibiotics, and instructions for use of the compositions.

DESCRIPTION OF THE DRAWINGS

For a fuller understanding of the nature and objects of the disclosure, reference should be made to the following detailed description taken in conjunction with the accompanying drawings. In the drawings or elsewhere in the disclosure, ALAFAC may be labeled as "HAMLET" or "HL".

Figure 6:
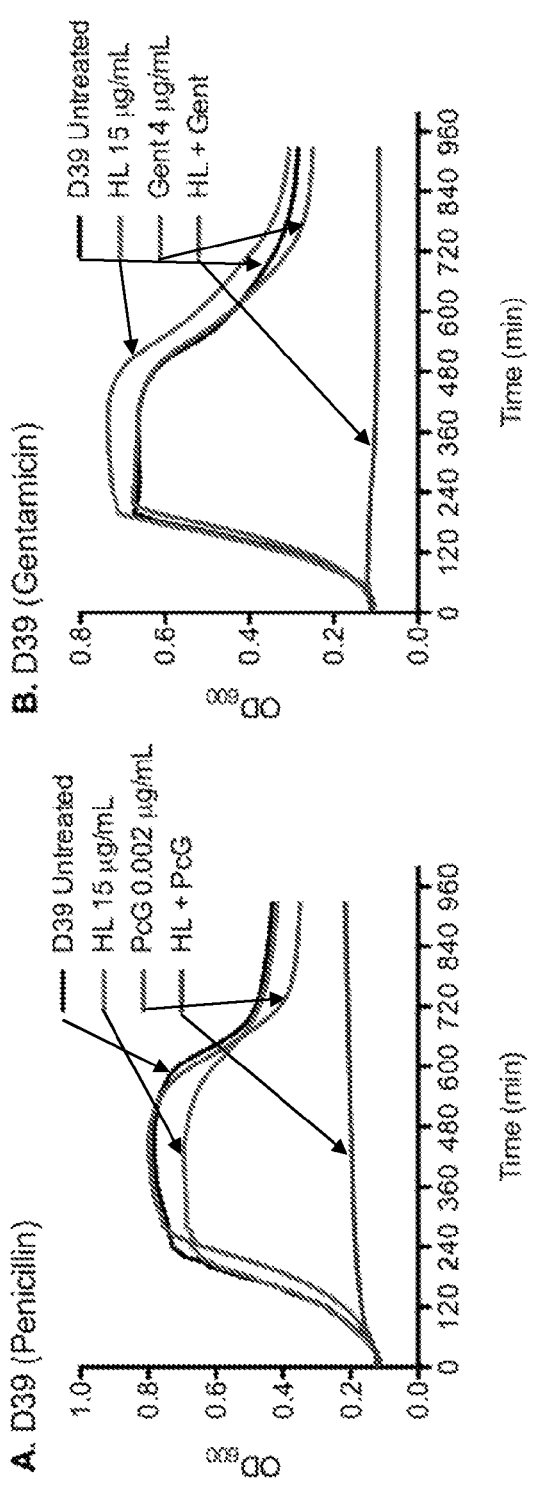

FIG. 6 shows an example of how ALAFAC (labeled as HL) lowers the MICs of gentamicin, erythromycin and penicillin S. pneumoniae D39 were grown in broth for 16 hours in the presence of penicillin G (A) or gentamicin (B) with and without the addition of ALAFAC. The figure shows representative growth curves for the lowest concentration of antibiotic and ALAFAC that inhibited bacterial growth by combination treatment without either agent alone affecting growth.

Figure 7:
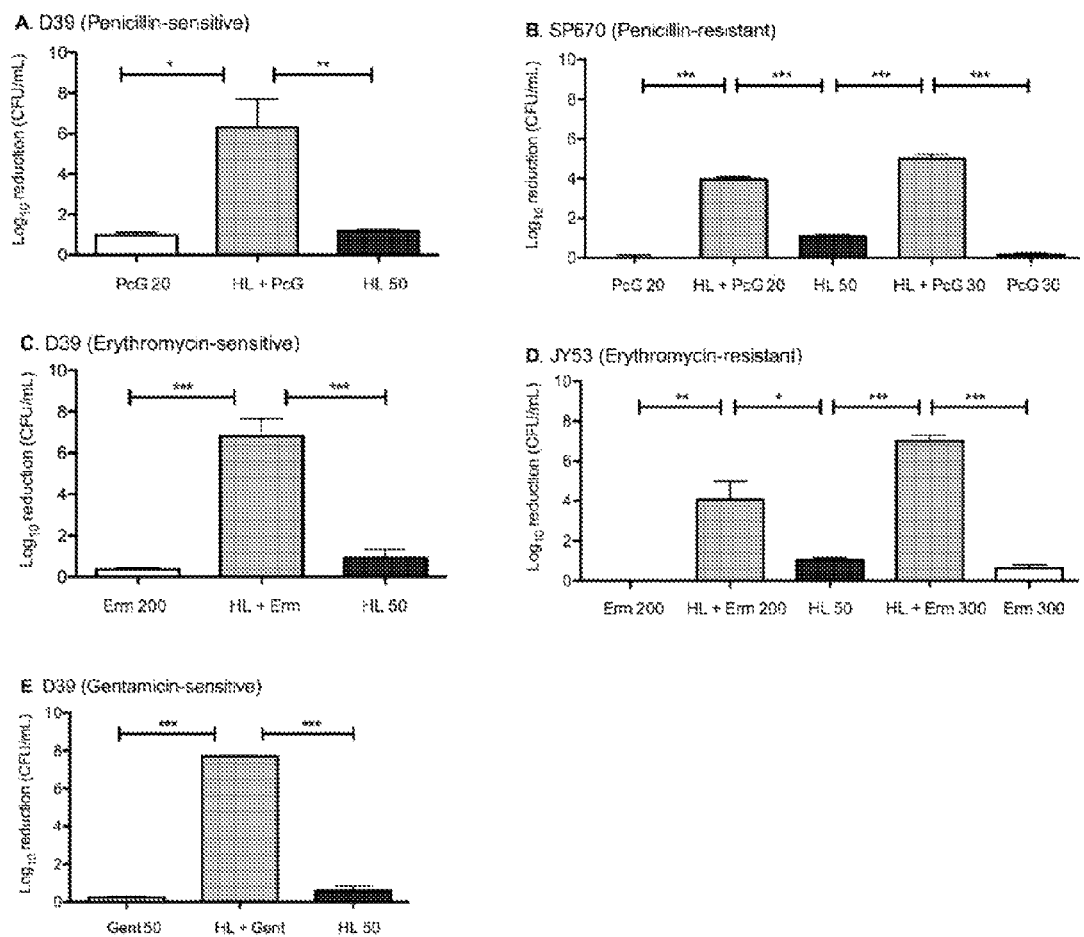

FIG. 7 shows a representative potentiation of short-time pneumococcal killing by gentamicin, penicillin and erythromycin in the presence of ALAFAC (labeled as HL). Short-time killing of the penicillin-sensitive strain D39 (A) by penicillin G (20 μg/mL), ALAFAC (50 μg/mL) and penicillin combined with ALAFAC over 4 hours. (B) Killing of the penicillin-resistant strain SP670 by penicillin G (20 or 30 μg/mL), ALAFAC (50 μg/mL), or penicillin G combined with ALAFAC over 4 hours. (C) Killing of the erythromycin-sensitive strain D39 by erythromycin (200 μg/mL), ALAFAC (50 μg/mL), or erythromycin combined with ALAFAC over 4 hours. (D) Killing of the erythromycin-resistant D39-derivative JY53 by erythromycin (200 μg/mL), ALAFAC (50 μg/mL), or erythromycin combined with ALAFAC over 4 hours. (E) Killing of D39 by gentamicin (50 μg/mL), ALAFAC (50 μg/mL), or gentamicin combined with ALAFAC over 1 hour. The results are based on three individual experiments with duplicate samples and are expressed as means±S.D. Statistics was performed using the unpaired Student t-test. Significance was indicated as follows: *=P<0.05, =P<0.01, *=P<0.001, ns=not significant.

Figure 8:
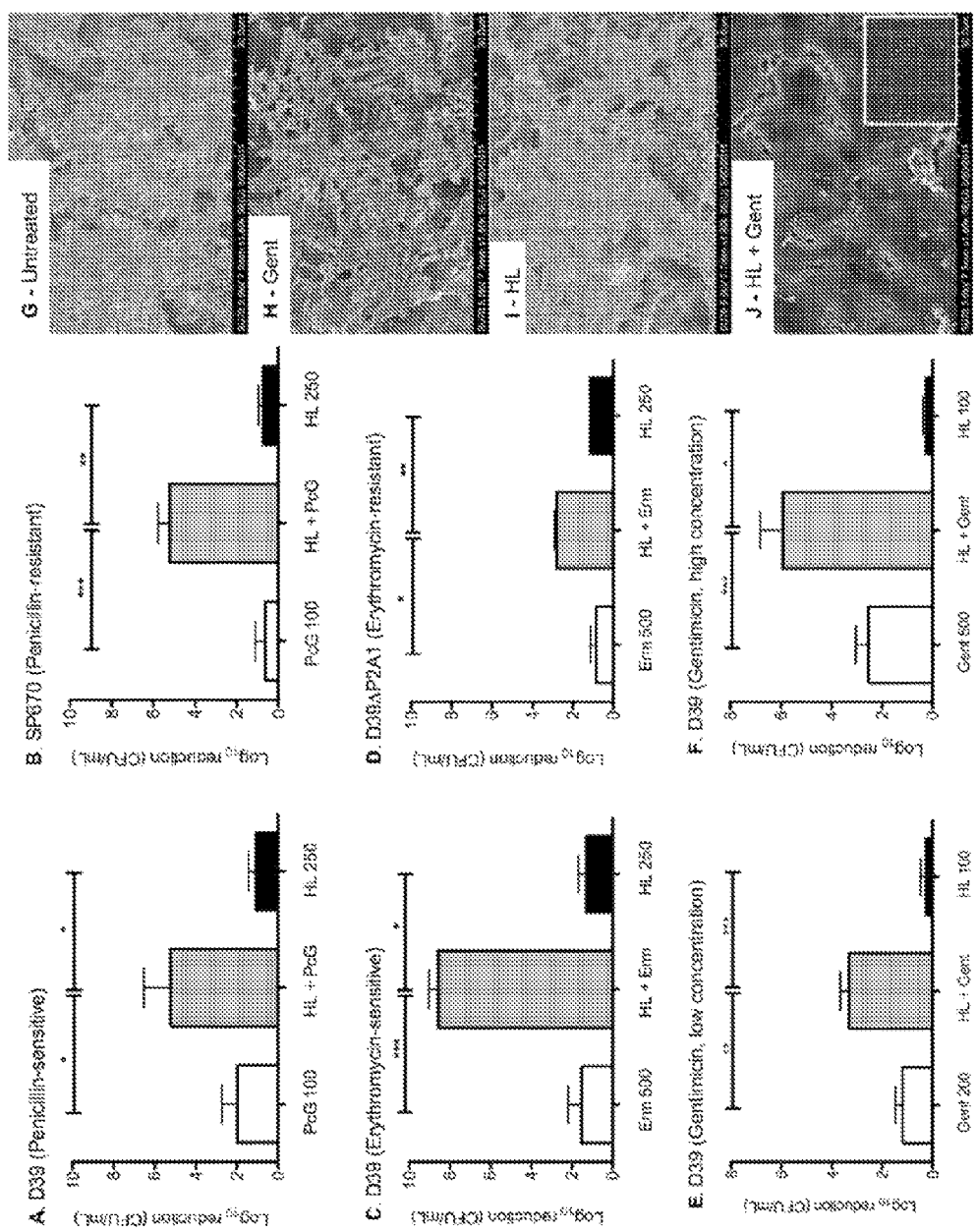

FIG. 8 shows a representative effect of ALAFAC (labeled as HL)/antibiotic combination treatment on in vitro biofilm viability. The activity of penicillin G (100 μg/mL), ALAFAC (250 μg/mL), or the combination of both agents were tested on in vitro biofilms of the penicillin-sensitive strain D39 (A) or the penicillin-resistant strain SP670 (B) formed over a prefixed epithelium of NCI-H292 cells and were tested by determining the bacterial death (in $\log_{10}$) after culturing bacterial dilutions overnight on blood agar. Similarly, the activity of erythromycin (250 μg/mL), ALAFAC (250 μg/mL), or the combination of both agents on in vitro biofilms of the erythromycin-sensitive strain D39 (C) or the erythromycin-resistant strain D39-P2A1 (D) were tested in a similar fashion as was the activity of 200 μg/ml gentamicin (E) or 500 μg/ml gentamicin (F) alone or in combination with 100 μg/ml ALAFAC (100 μg/mL) over 3 hours on pre-established biofilms formed by the strain EF3030. The results are based on three individual experiments with duplicate samples. Statistics was performed using the paired Student t-test. Significance was indicated as follows: *=P<0.05, **=P<0.01. To visualize the morphology of the treated biofilms, SEM studies were performed. Images show (G) the structure of an untreated 48 hour EF3030 biofilm, (H) an EF3030 biofilm after 3 hour treatment with 500 μg/mL gentamicin alone, (I) an EF3030 biofilm after 3 hour treatment with ALAFAC (100 μg/mL) alone and (J) an EF3030 biofilm after 3 hour treatment with the combination of 100 μg/mL ALAFAC and 500 μg/mL Gentamicin. An epithelial substratum prior to biofilm formation has been included as a control (insert in panel J). The increased bactericidal activity of the combination treatment was associated with a reduction in the density of adherent bacteria and biofilm matrix.

Figure 9:
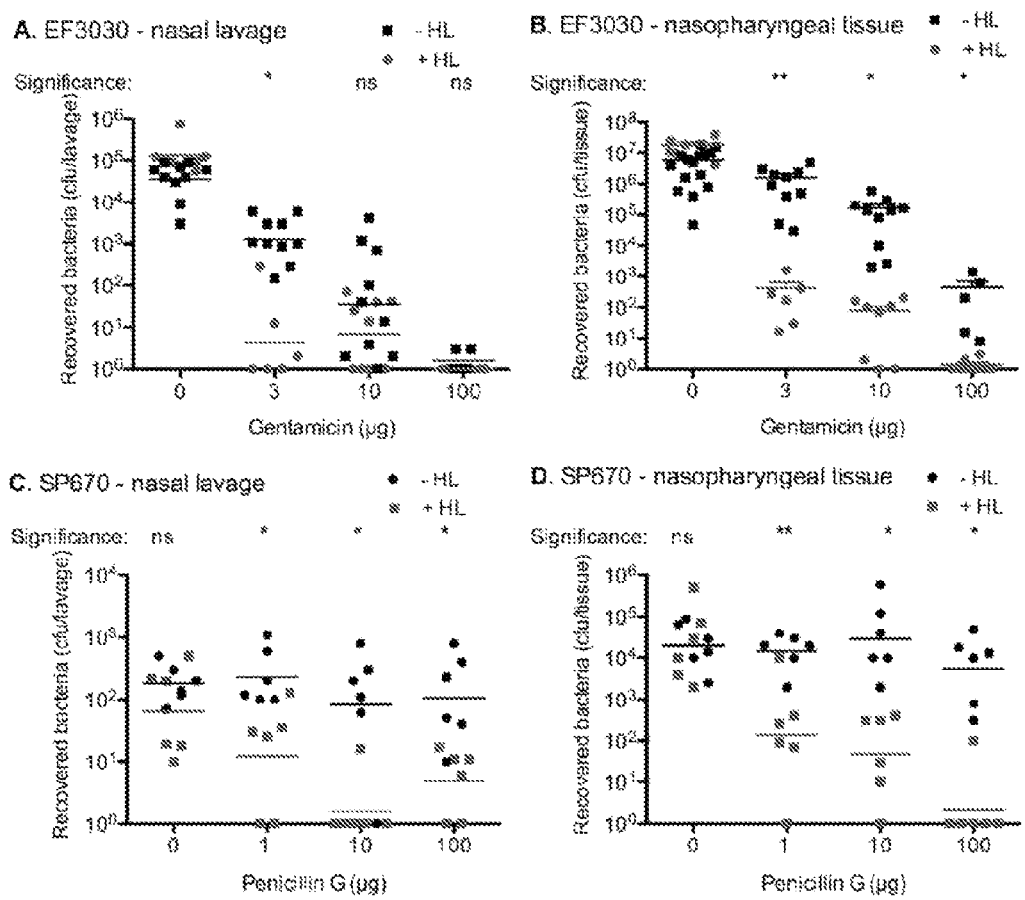

FIG. 9 shows a representative ALAFAC (labeled as HL)-antibiotic combination treatment eradicates pneumococci during nasopharyngeal colonization. (A and B) Mice were colonized with S. pneumoniae EF3030 for 48 hours, treated intranasally with various doses of gentamicin in the presence (circles) or absence (squares) of ALAFAC (50 μg) for 6 hours, and the bacterial burden associated with the nasal lavage (A) and the nasopharyngeal tissue (B) was determined Bacteria in nasal lavage and associated with the nasopharyngeal tissue were significantly more sensitive to gentamicin/ALAFAC combination therapy than gentamicin alone. (C and D) Mice were colonized with the penicillin-resistant strain S. pneumoniae SP670 (MIC=4 μg/mL) for 48 hours, treated intranasally with various doses of penicillin G in the presence (circles) or absence (squares) of ALAFAC (50 μg) for 12 hours and the bacterial burden associated with the nasal lavage (C) and the nasopharyngeal tissue (D) was determined Penicillin G alone had no effect on the bacterial burden in either the nasal lavage or in the tissue. However, combination therapy with ALAFAC and penicillin caused a dose-dependent decrease in bacterial burden leading to eradication of colonization. The graph shows colonization data for individual mice, with the mean recovered bacteria and the standard deviation depicted. The results are based on experiments using groups of 6-10 mice. Statistics was performed using the unpaired Student t-test. Significance was indicated as follows: *=P<0.05, **=P<0.01, ns=non-significant.

Figure 10:
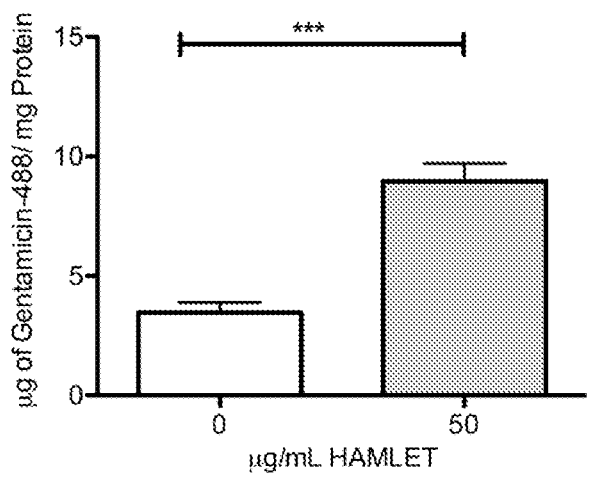
Figure 10:
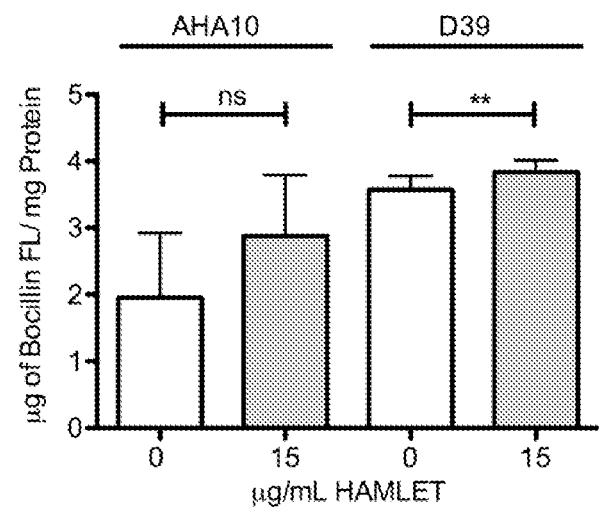

FIG. 10 shows an example of the impact of ALAFAC (labeled as HAMLET) on uptake and binding of gentamicin and Bocillin FL. (A) S. pneumoniae D39 were incubated with Alexa Fluor 488-gentamicin in the presence or absence of ALAFAC. ALAFAC significantly increased the cell-associated level of gentamicin. (B) The penicillin-resistant strain SP670 and the penicillin-sensitive strain D39 were incubated with the fluorescent beta-lactam Bocillin FL in the presence or absence of ALAFAC. ALAFAC did not increase the cell-associated level of Bocillin FL in either strain. The results are based on three individual experiments with duplicate samples. Statistics was performed using the unpaired Student t-test. Significance was indicated as follows: =P<0.01, *=P<0.001, ns=not significant.

Figure 11:
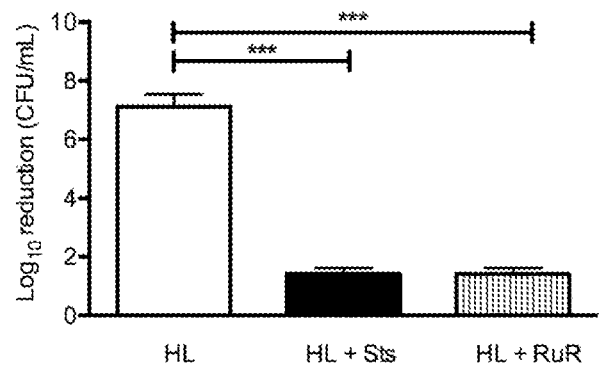
Figure 11:
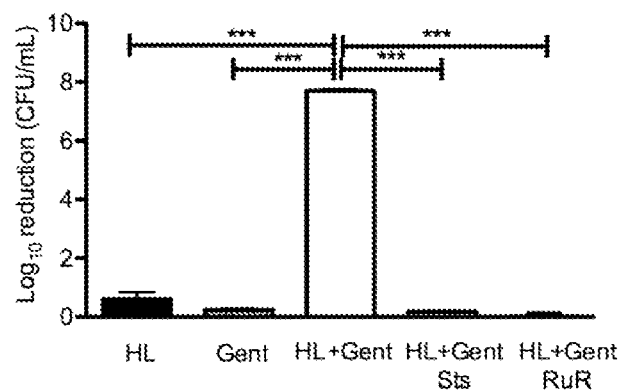
Figure 11:
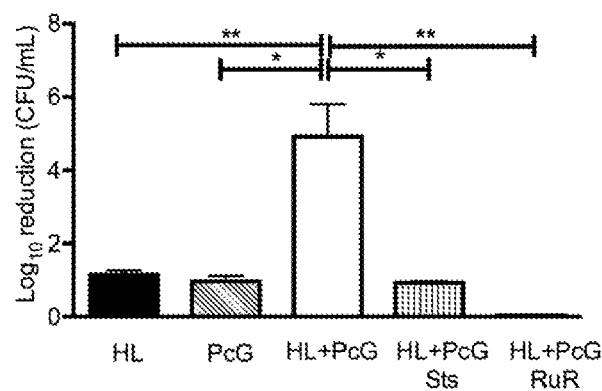

FIG. 11 shows an example of the effect of calcium and kinase inhibitors on ALAFAC (labeled as HAMLET or HL)-induced sensitization of pneumococci to gentamicin. (A) S. pneumoniae D39 were treated with a lethal concentration of ALAFAC (12×MIC) in the absence of inhibitor (HL) or presence of 20 μM staurosporine (HL+Sts), or 30 μM ruthenium red (HL+RuR) for 1 hour at 37° C. The treated bacteria were diluted and plated on blood agar plates and viable CFU/ml were determined after overnight growth. (B and C) *S. pneumoniae* D39 were treated with 50 μg/mL ALAFAC (HL), 50 μg/mL gentamicin (Gent), 20 μg/mL penicillin G (PcG), or a combination of gentamicin and ALAFAC or penicillin G and ALAFAC in the absence (HL+Gent, HL+PcG) or presence of 20 μM staurosporine (Sts), or 30 μM ruthenium red (RuR) for 1 hour at 37° C. The treated bacteria were diluted and plated on blood agar plates and viable CFU/ml were determined after overnight growth. The graph depicts the $\log_{10}$ death induced by each treatment and showed that staurosporine and ruthenium red significantly reduced ALAFAC-induced death (A) and also significantly blocked ALAFAC's ability to sensitize pneumococci to gentamicin (B) and penicillin G (C). The results are based on three individual experiments with duplicate samples. Statistics was performed using the unpaired Student t-test. Significance was indicated as follows: ***=P<0.001.

Figure 12:
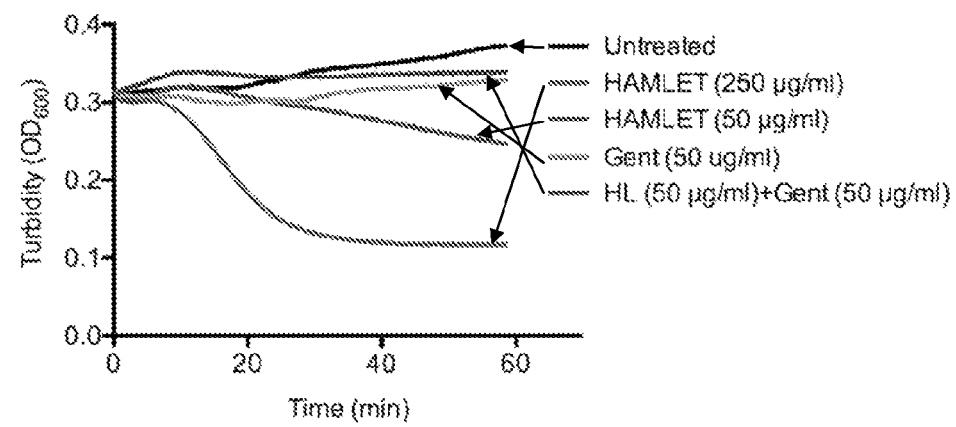
Figure 12:
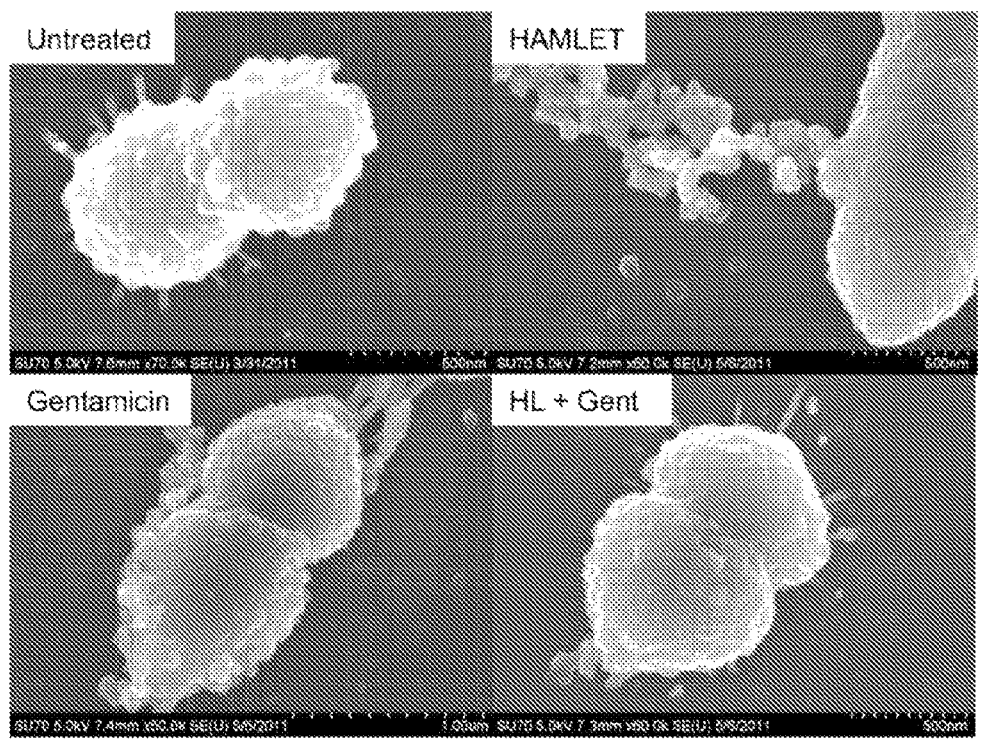

FIG. 12 shows a representative autolysis during ALAFAC (labeled as HAMLET or HL)-gentamicin combination therapy. (A) Optical density at 600 nm of *S. pneumoniae* D39 after exposure to a lethal concentration of ALAFAC (250 μg/ml), a sublethal concentration of ALAFAC (50 μg/ml), a sublethal concentration of gentamicin (50 μg/mL) or the combination of sublethal concentrations of ALAFAC and gentamicin that resulted in complete death of the inoculum. The data shows a representative experiment. (B) Representative scanning electron micrographs of untreated *S. pneumoniae* D39, as well as bacteria treated 4 minutes with a lethal concentration of ALAFAC (250 μg/mL), one hour with a similarly lethal concentration of gentamicin (500 μg/mL) or one hour with a sublethal concentration of ALAFAC (50 μg/mL) or a sublethal concentration of gentamicin (50 μg/mL) in combination (HL+Gent). Note the numerous defects of the pneumococcal cell wall after exposure to ALAFAC or gentamicin alone compared with the structurally intact cells after exposure to the combination of the two agents.

Figure 13:
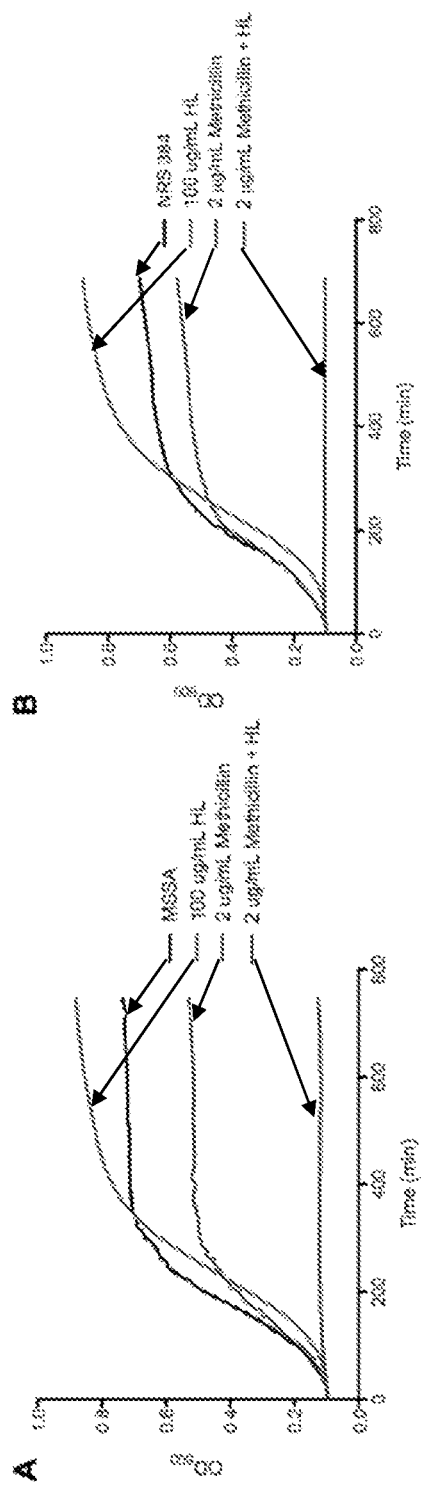

FIG. 13 shows an example of how ALAFAC (labeled as HL) lowers the methicillin MIC. *S. aureus* strains 11090306 (MSSA) (left) and NRS 384 (MRSA) (right) were grown in broth for 16 hours in the presence of 2 μg/ml methicillin (5 μM) with and without the addition of 100 μg/mL (6 μM) ALAFAC. The figure shows representative growth curves for the lowest concentration of antibiotic and ALAFAC that inhibited bacterial growth by combination treatment without either agent alone affecting growth.

Figure 14:
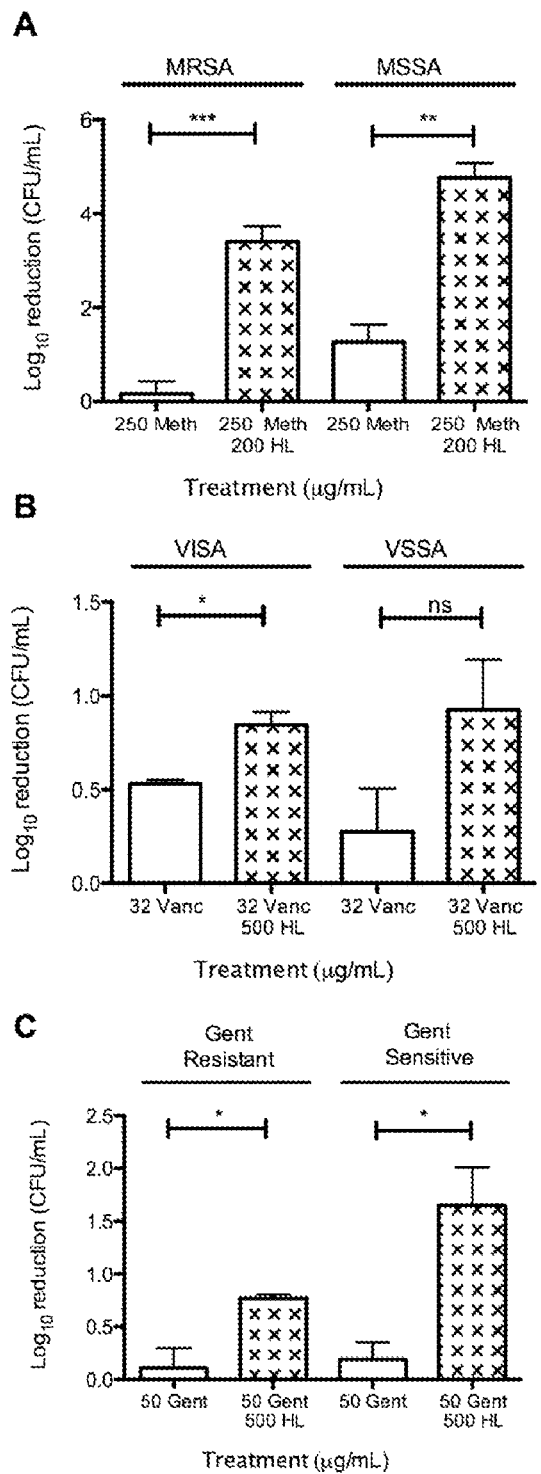

FIG. 14 shows a representative effect of ALAFAC (labeled as HL)/antibiotic combination treatment on in vitro biofilm viability. (A) The activity of methicillin (250 μg/mL or 660 μM), ALAFAC (200 μg/mL or 12 μM), or the combination of both agents were tested on in vitro biofilms of the methicillin-resistant strain NRS 70 (MRSA) or the methicillin-sensitive strain 11090306 (MSSA) by determining the bacterial death (in $\log_{10}$) after culturing dilutions overnight on blood agar. (B) The activity of vancomycin (32 μg/mL or 21 μM), ALAFAC (500 μg/mL or 30 μM), or the combination of both agents on in vitro biofilms of the vancomycin-resistant strain NRS 1 (VISA) and the vancomycin-sensitive strain NRS384 (VSSA) were tested in a similar fashion as was the activity of (C) 50 μg/ml (105 μM) gentamicin alone or in combination with 500 μg/ml (30 μM) ALAFAC for the gentamicin-resistant strain. The results are based on three independent experiments with duplicate samples. Statistics was performed using the paired Student t-test. Significance was indicated as follows: ns=not significant, *=P<0.05, **=P<0.01.

Figure 15:
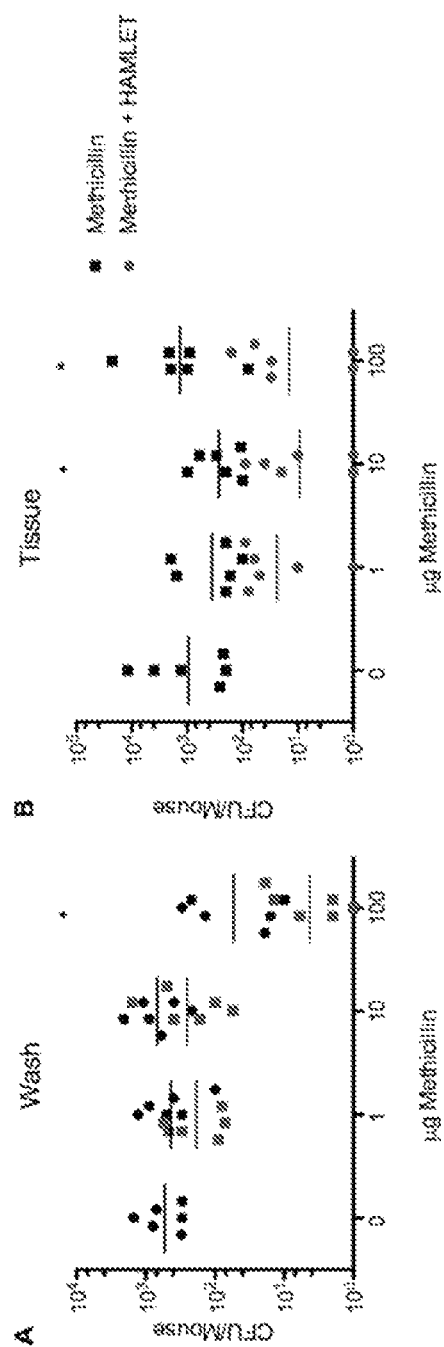

FIG. 15 shows an example of how ALAFAC (labeled as HAMLET)/Methicillin combination treatment reduces Staphylococcal nasopharyngeal colonization. Mice were colonized with *S. aureus* NRS 70 for 24 hours, treated intranasally with various doses of gentamicin in the presence (squares) or absence (circles) of ALAFAC (100 μg) for 12 hours, and the bacterial burden associated with the nasal wash (A) and the nasopharyngeal tissue (B) was determined. The graph shows colonization data for individual mice, with the mean recovered bacteria depicted with a line. The results are based on experiments using groups of 6 mice. Statistics was performed using the unpaired Student t-test. Significance was indicated as follows: *=P<0.05.

Figure 16:
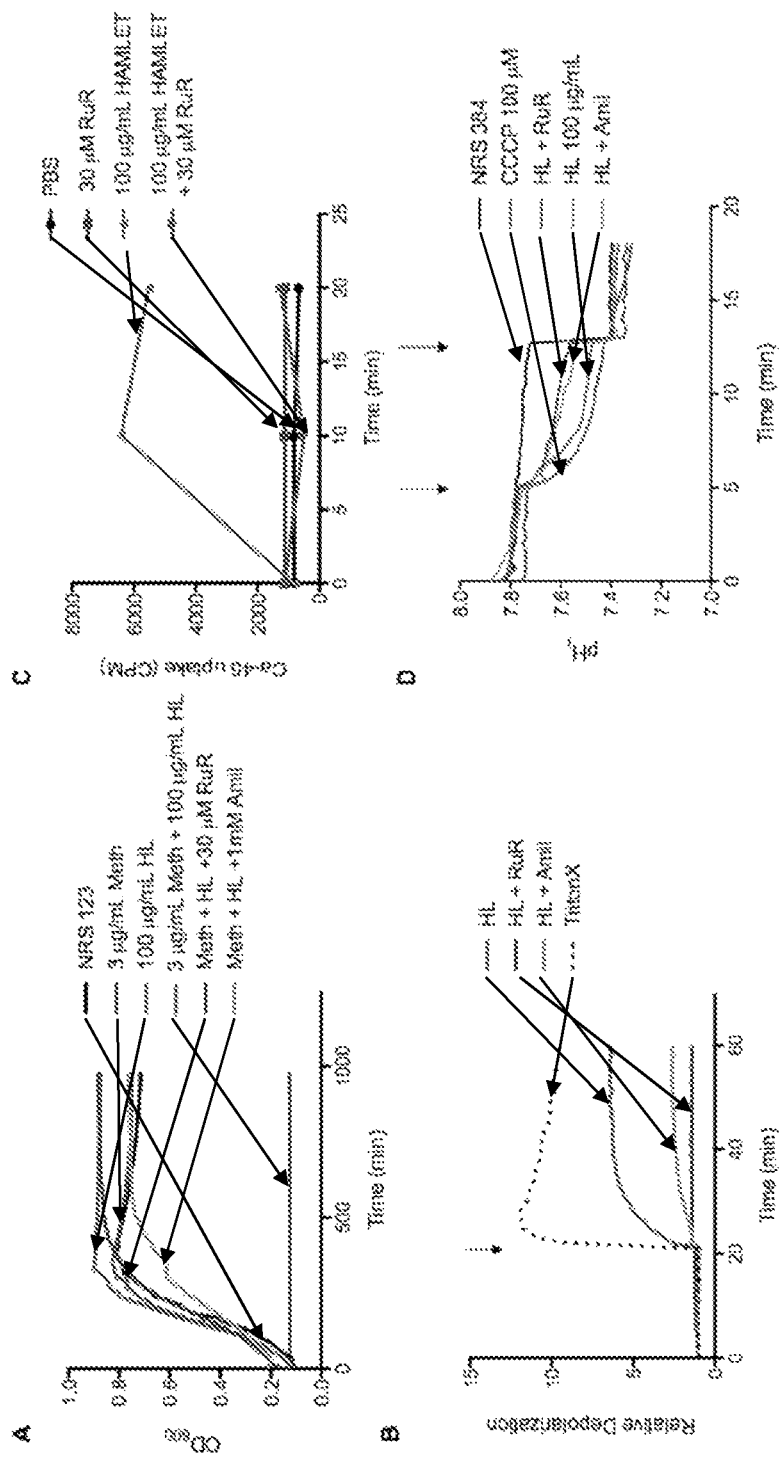

FIG. 16 shows a representative effect of ALAFAC (labeled as HAMLET or HL) on membrane potential. (A) Representative growth curves for *S. aureus* strain NRS 123 (MRSA) grown in broth for 16 hours (960 min) in the presence of methicillin with and without the addition of ALAFAC and the inhibitors Ruthenium Red (RuR) or Amiloride (Amil) (B) Mid-log phase grown NRS 123 Staphylococci re-suspended in PBS alone or PBS plus Amiloride or Ruthenium Red, were incubated with the fluorescent indicator dye DiBAC$_4$(3) and membrane depolarization was detected by measuring fluorescence over time. ALAFAC was added at twenty minutes (arrow). The detergent Triton X-100 (0.1%) was included as a positive control. The results presented are from one representative experiment. (C) Mid-log phase grown NRS 384 Staphylococci were incubated with the radioisotope $^{45}Ca^{2+}$ (2.5 μCi/mL) in PBS or PBS+Ruthenium Red (30 μM). After recording baseline readings, PBS (untreated), or ALAFAC was added (Time=0 min) to the bacteria and radioactivity was measured over time. Results from a representative experiment are shown. (D) NRS 384 Staphylococci were loaded with the pH sensitive dye BCECF-AM, and were washed and resuspended in PBS+25 mM glucose. After recording baseline readings, at the first arrow, PBS (untreated), the protonophore CCCP (100 μM), ALAFAC (100 μg/mL or 6 μM), ALAFAC+RuR (30 μM), or ALAFAC+ Amiloride (1 mM) were added to the bacteria and fluorescence was measured over time. At the second arrow 20 μM each of nigericin and valinomycin was added to completely dissipate the transmembrane proton gradient.

Figure 17:
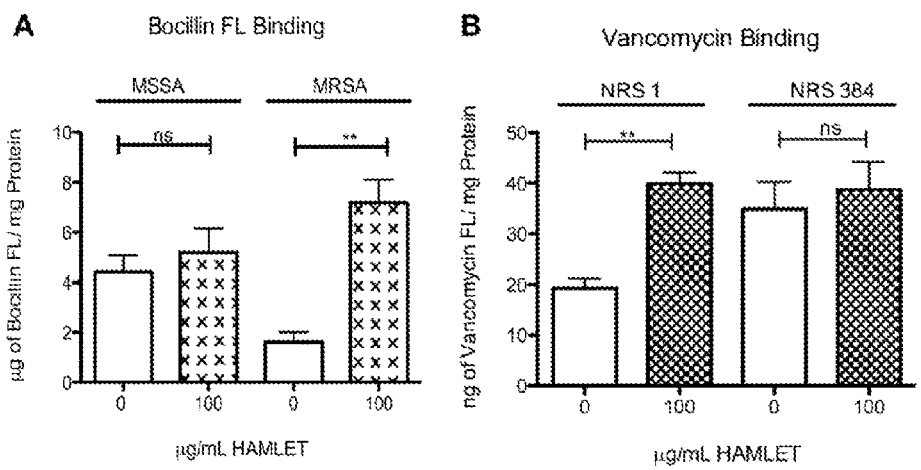

FIG. 17 shows a representative impact of ALAFAC (labeled as HAMLET) on uptake and binding of Bocillin FL and vancomycin FL. (A) Staphylococci were incubated with Bocillin FL or (B) with vancomycin FL in the presence or absence of 100 μg/mL (6 μM) ALAFAC. The results are based on three individual experiments with duplicate samples. Statistics was performed using the unpaired Student's t-test. Significance was indicated as follows: =P<0.01, *=P<0.001, ns=not significant.

Figure 18:
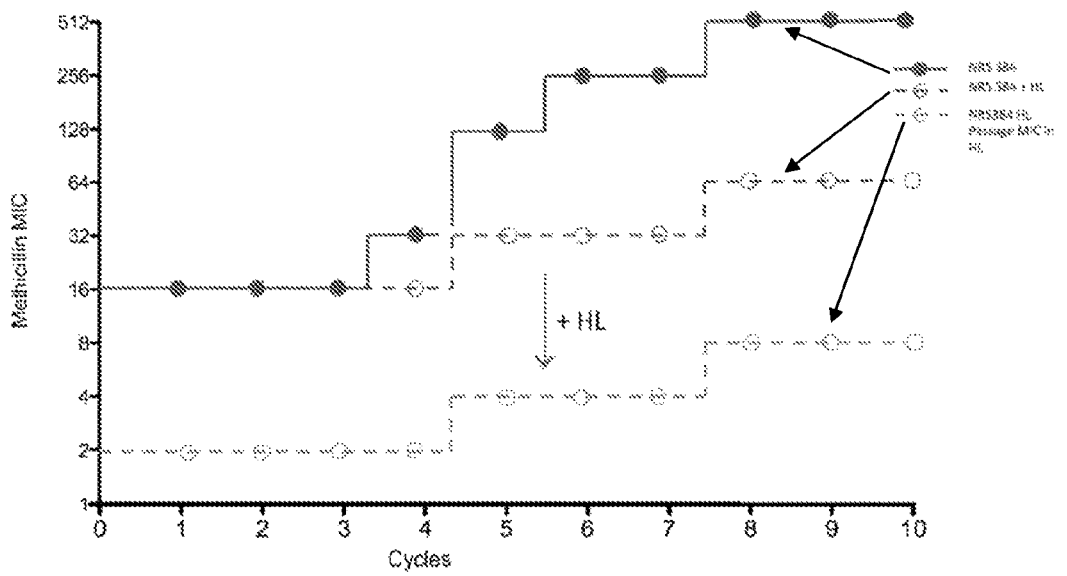

FIG. 18 shows an example of ALAFAC (labeled as HL) and resistance development. Methicillin adaptation of the MRSA strain NRS 384 after exposure to stepwise increasing concentrations of methicillin alone (1-512 μg/mL or 2.5-1, 350 μM) or methicillin in combination with 100 μg/mL (6 μM) ALAFAC. The filled circles (labeled NRS 384) show the methicillin MICs after each cycle when no ALAFAC was used. The addition of 100 μg/mL of ALAFAC reduced methicillin-induced resistance (unfilled circles labeled NRS 384+HL). The unfilled circles labeled NRS384 HL Passage MIC in HL represents the MIC of methicillin of the bacteria grown in presence of ALAFAC, when ALAFAC was also present during the MIC assay to potentiate the effect of the antibiotic. Reintroduction of ALAFAC to these isolates again returned the methicillin MIC back to the levels denoted by the unfilled circles labeled NRS384 HL Passage MIC in HL.

DETAILED DESCRIPTION OF THE DISCLOSURE

A novel complex of α-lactalbumin and fatty acid in human milk was previously identified (Hakansson et al., 1995, Proc Natl Acad Sci USA 92:8064-8068; Svensson, et al., 2000, Proc Natl Acad Sci USA 97:4221-4226). A non-covalent complex of alpha-lactalbumin and fatty acid is hereinafter referred to as alpha-lactalbumin fatty acid complex or ALAFAC. The complex purified from the casein fraction of human milk, was found to be made up of alpha-lactalbumin in a partially unfolded conformation that could be stabilized under physiological conditions by a human derived fatty acid fraction containing oleic acid and linoleic acid. This protein-lipid complex was found to have limited bactericidal effect against only a few respiratory tract pathogens (Hakansson et al., 2000, Mol Microbiol 35:589-600). For example, while ALAFAC has bactericidal effect against the respiratory tract pathogens Streptococcus pneumoniae, Haemophilus influenzae, and some strains of Moraxella catarrhalis, it showed no detectable activity even at concentrations up to 5 mg/ml against gram-positive organisms such as Staphylococci and Bacillus subtilis and against the gram-negative organisms Escherichia coli and Pseudomonas aeruginosa.

The present disclosure is based on the unexpected finding that ALAFAC can potentiate anti-bacterial activity of antibiotics. This potentiating or synergistic effect is seen against bacteria, which are sensitive to ALAFAC as well as in bacteria which are not sensitive to ALAFAC. Further, the potentiation of the anti-bacterial effect of antibiotics is seen against bacteria that are sensitive to the antibiotics and also with bacteria that are resistant to antibiotics.

ALAFAC can be isolated from biological materials or can be prepared by complexing fatty acids and alpha-lactalbumin. For example, ALAFAC can be isolated from the milk of primates, including humans. It can also be prepared by complexing ALA with fatty acids. See, e.g., U.S. Pat. Nos. 6,808,930, 7,053,185, and 7,524,932, which are incorporated herein by reference. The alpha-lactalbumin can be obtained from any mammalian source (such as milk), including but not limited to, primates, cattle, rodents, and the like. For example, it can be obtained from humans, cows, dogs, goats, sheep, horses, and the like. Alpha-lactalbumin is also available commercially (such as from Sigma Aldrich). In one embodiment, alpha-lactalbumin can also be produced by recombinant methods. See, e.g., Svensson et al., 2000, Proc Natl Acad Sci USA 97:4221-4226. Genbank accession number for human ALA is NP_002280.1; GI:4504947). Genbank accession numbers for ALA from other species are: Cow: NP_776803.1 GI:27805979; Horse: P08334.2 GI:125991, Donkey: AAB24573.1 GI:262063, Sheep: NP_001009797.1 GI:57526478, Goat: CAA28797.1 GI:980, Pig: NP_999525.1 GI:47523778, and Dog: NP_001003129.1 GI:50978848.

Fatty acids useful for making the ALAFAC complex include unsaturated cis C14 to C20 fatty acids. In one embodiment, the fatty acids are C16 and C18 fatty acids. In one embodiment, the fatty acids are oleic acid and/or linoleic acid. In one embodiment, the milk fraction containing oleic acid and/or linoleic acid is obtained from the milk of primates, such as humans. This milk is known to be high in oleic and linoleic acid. Milk from other mammals is known to be rich in smaller fatty acids (such as C14 or lower) and is not known to contain significant amounts of C18 or C16 fatty acids. In one embodiment, commercially available C18 or C16 can also be used. Additionally, several vegetable oils (such as olive oil) are known to be a rich source of oleic and linoleic acids.

In one embodiment, ALAFAC can be isolated as described in U.S. Pat. Nos. 6,808,930; 7,053,185 and 7,524,932, the disclosures of which with respect to isolation of ALAFAC are incorporated herein by reference. For example, it can be purified from milk by removal of fat (such as by centrifugation), and separation into casein and whey (such as by acid precipitation). The separated casein is harvested (such as by centrifugation) and washed. The casein fraction can be fractionated (such as by using ion exchange chromatography) and elutes with salt (such as 1M NaCl). The eluent can then be desalted against distilled water. In one embodiment, ALAFAC can be isolated from human milk or may be produced by exposing milk-derived or recombinant apo-ALA (EDTA-treated) to oleic acid bound to a DEAE matrix using fast protein liquid chromatography or by loading lipid to the protein under alkaline conditions.

In one embodiment, the ALAFAC complex has from 1 to 40 (and all integers therebetween) fatty acid molecules complexed to a molecule of ALA. In various embodiments, the ALAFAC complex has 35 or less, 30 or less, 25 or less, 20 or less, 15 or less, or 10 or less fatty acid molecules complexed to a molecule of ALA. In one embodiment, the ALAFAC has from 1 to 15 fatty acid molecules complexed to a molecule of ALA. In one embodiment, there are from 5 to 10 fatty acid molecules complexed to a molecule of ALA. In one embodiment, the toxicity of ALAFAC when there were 10 or less fatty acid molecules complexed to a molecule of ALA, was found to be acceptable. In various embodiments, the ALAFAC complex comprises 1, 2, 3, 4, 5, 6, 7, 8, 9, 10, 11, 12, 13, 14, or 15 oleic acid and/or linoleic acid molecules complexed to a molecule of ALA.

The ALAFAC can be stored in the refrigerator or can be frozen. For example, ALAFAC can be stored in physiological buffer (such as 0.9% saline or phosphate buffered saline) at 4° C. for at least 3 months and stability is maintained in solution for over 1 year. If can also be stored at room temperature for at least three weeks.

In one embodiment, the components for forming ALAFAC may be provided separately. For example, alpha-lactalbumin and fatty acids may be provided separately and may be combined in a suitable buffer (such as physiological buffer) to effect the formation of the complex. Generally, ALA in the unfolded form will non-covalently bind to fatty acids. In one embodiment, the fatty acids and ALA are provided such that from 1 to 40, 1 to 30, 1 to 20 or 1 to 10 fatty acids may bind to each ALA molecule.

By the term "no bactericidal effect" or "anti-bacterial effect", it is meant that no detectable effect on the growth or survival of bacteria is observed. For bacteria considered resistant to an antibiotic, no bactericidal effect is observed at up to 5 mg/ml when tested in vitro. Alternatively, bacteria may be deemed resistant to an antibiotic because no improvement is seen clinically in a patient's condition upon administration of a full regimen of that antibiotic. Conversely, bacteria are considered to be sensitive to an antibiotic when bactericidal activity can be detected at therapeutically effective ranges or when an improvement is seen in a patient's condition upon administration of a full regimen of that antibiotic.

In one embodiment, the present disclosure provides compositions and methods for potentiating the effects of antibiotics against bacteria, which are known to be antibiotic resistant. In this embodiment, the potentiation is in the form of conferring sensitivity toward an antibiotic against which the bacteria was previously resistant. Those skilled in the art will recognize that the concentrations at which antibiotics are effective against various bacteria depends upon the type of bacteria. Determination of such ranges is within the purview of one skilled in the art. For example, penicillin sensitivity can be seen at 0.1 μg/ml. In one embodiment, the amount of antibiotic effective against sensitive strains is in the range of 0.2 to 250 μg/ml. In various embodiments, the concentration of antibiotics when used with ALAFAC is from 0.1 to 1.0 mg/ml and all concentrations to the tenth decimal place therebetween. In some embodiments, the concentration is from 1 to 500 μg/ml and all values to the tenth decimal place therebetween.

In another embodiment, the present disclosure provides compositions and methods for potentiating the effects of antibiotics against bacteria, which are sensitive to antibiotics. In this embodiment, potentiation is in the form of reducing the amount of an antibiotic that is needed to treat the infection compared to the amount needed without ALAFAC. In various embodiments, the concentration of antibiotics when used with ALAFAC is from 0.1 to 1.0 mg/ml and all concentrations to the tenth decimal place therebetween. In some embodiments, the concentration is from 1 to 500 μg/ml and all values to the tenth decimal place therebetween. In some embodiments, the antibiotic needed to treat the infection is 2 to 300 (and all integers therebetween) fold less than the amount required without ALAFAC.

The potentiation of the effect of antibiotics may be seen as a decrease in the MIC or short-kill assay times for in vitro studies. The potentiation may also be seen in the form of improvement of an individual's condition, for example, as determined by a clinician. The combination of ALAFAC complex and an antibiotic may decrease the MIC, reduce the short-kill time for bacteria which are sensitive or resistant to ALAFAC and/or the antibiotic. Determination of MICs is well within the purview of those skilled in the art. Further MIC values for different antibiotics and different bacteria can be obtained from the Antimicrobial Index at http://antibiotics.toku-e.com. In various embodiments, the MIC for antibiotics is reduced from 2 to 300 (and all integers therebetween) fold upon use with ALAFAC.

For example, it was observed that ALAFAC potentiates the action of antibiotics in ALAFAC-resistant bacteria and that it works equally well or even better for pneumococci (ALAFAC sensitive). It was observed that a combination of ALAFAC and gentamicin, penicillin or erythromycin, significantly enhanced bacterial killing against both antibiotic sensitive and antibiotic resistant organisms in vitro and in vivo. For example, addition of ALAFAC to gentamicin resulted in a 10-fold reduction in the dose needed to eradicate both lavage- and tissue-associated gentamicin-tolerant pneumococci in an animal model and addition of ALAFAC to penicillin resulted in a 33-fold reduction in the dose needed to eradicate colonization by the penicillin-resistant strain SP670 that was completely insensitive to penicillin alone. It was also found that the gram-negative respiratory organisms *A. baumanii* and *M. catarrhalis*, both of which show a high level of antibiotic resistance against beta-lactams and other classes of antibiotics and are also resistant to ALAFAC, showed that the MIC for penicillin and gentamicin were significantly reduced. Thus, ALAFAC can provide a way to increase the usefulness of existing drugs, and extend the lifetime of the current treatment arsenal antibiotic resistant also in ALAFAC-resistant organisms.

Examples of bacteria against which ALAFAC by itself has shown bactericidal activity are: *Streptococcus pneumoniae, Haemophilus influenzae*, and some strains of *Moraxella catarrhalis*, although the effect against *Moraxella catarrhalis* is generally poor and less than 90% reduction occurs at 2 mg/ml. Examples of bacteria against which it showed no detectable activity, even at concentrations up to 5 mg/ml, are gram-positive organisms, such as Staphylococci and *Bacillus subtilis*, and gram-negative organisms, such as *Escherichia coli* and *Pseudomonas aeruginosa*. The present compositions and methods are useful for all Gram-positive and Gram-negative bacteria, and for antibiotic resistant as well as antibiotic sensitive bacteria. Examples of Gram positive bacteria include, but are not limited to, *Streptococcus pneumonia, Staphylococcus aureus, Staphylococcus epidermidis, Streptococcus sanguis, Streptococcus mutans, Streptococcus pyogenes* (Group A), *Streptococcus agalactiae* (Group B), and *Enterococcus faecalis*. Examples of Gram negative bacteria include, but are not limited to, *Escherichia coli, Haemophilus* influenza, *Haemophilus parainfluenzae, Moraxella catarrhalis, Acinetobacter baumanii, Klebsiella pneumonia, Pseudomonas aeruginosa*, and *Enterobacter cloache*.

In one aspect, the present disclosure provides compositions for use as adjuvant. In one embodiment, the adjuvant composition comprises, or consists essentially of, ALAFAC at an amount sufficient to act as an adjuvant. For bacteria against which ALAFAC itself has a bactericidal effect (ALAFAC sensitive bacteria), the amount at which it can exert its adjuvant effect is lower than the amount at which it exerts its bactericidal effect. In one embodiment, the composition comprises ALAFAC at an amount sufficient to act as an adjuvant and the composition may have bactericidal activity.

In one embodiment, the compositions for use as adjuvants for potentiating the activity of antibiotics are suitable for administration to individuals. In one embodiment, the compositions are sterile and packaged in sterile packaging or containers. In one embodiment, the compositions do not contain other proteins or amino acids. In one embodiment, the compositions do not contain serum albumin and/or essential amino acids. In one embodiment, the compositions do not contain vitamins. In one embodiment, the compositions do not contain growth factors or hormones. In one embodiment, the compositions are free of serum albumin and other serum proteins, essential amino acids, growth factors, hormones, and vitamins.

The concentration of ALAFAC may be 0.1 μg/ml to 10.0 mg/ml and all concentrations to the tenth decimal place therebetween. In some embodiments, the concentration of ALAFAC for use with ALAFAC sensitive bacteria may be from 0.1 μg/ml to 100 μg/ml and all concentrations to the tenth decimal place therebetween. In some embodiments, the concentration of ALAFAC for use with bacteria resistant to ALAFAC may be from 0.1 μg/ml to 5.0 mg/ml and all concentration therebetween to the tenth decimal place, and for use with bacteria sensitive to ALAFAC may be from 0.1 μg/ml to 1.0 mg/ml and all concentration therebetween to the tenth decimal place.

In one embodiment, the adjuvant composition is provided in doses or portions such that each dose or portion provides a sufficient dose for administration to an individual, wherein the total amount in the aliquots or portions (for a complete dosage regimen) is sufficient to act as an adjuvant to the activity of an antibiotic, but will not have bactericidal activity by itself i.e., without the antibiotic. The total doses required for a treatment regimen are referred to herein as a "treatment set". For example, a treatment regimen for many antibiotics typically contains doses that are taken over a period of 5 to 10 days. Thus, if ALAFAC is to be administered over the same period of time, then a treatment set for ALAFAC may comprise doses to be administered over the 5 or 10 days. Each portion or dose may be suitable for topical, oral, intravenous or any other form of administration. Each portion or dose may be packaged in a discrete compartment (such as tablets in a blister packaging, or a topical patch/bandage in a containment) or may be packaged as bulk (such as ointment in a tube or suspension in a bottle). In various embodiments, such adjuvant amounts may be 2 to 300 times (and all integers therebetween) lower than the amounts that would be bactericidal to sensitive bacteria. In one embodiment, the amount is 2-100 times or 2-10 times lower that the amounts that would be bactericidal to sensitive bacteria.

In one embodiment, the compositions comprise, or consists essentially of, ALA, fatty acids and a suitable buffer in amounts suitable for combining such that ALAFAC may be formed by the complexing of ALA with the fatty acids. In one embodiment, the amount of fatty acid is such that from 1 to 40 (and all integers therebetween) fatty acid molecules can be complexed with each ALA.

In another embodiment, the present disclosure provides compositions comprising ALAFAC and one or more antibiotics. In one embodiment, the composition comprises ALA, fatty acid(s), and one or more antibiotics. The antibiotic may be any antibiotic that is useful for treating infections. For example, the antibiotic may be a broad spectrum antibiotic or may be effective against particular bacteria. In various embodiments, the composition comprises or consists essentially of, i) ALAFAC, and/or ii) fatty acids and ALA, and iii) one or more antibiotics, all in suitable carriers or buffers.

Suitable antibiotics include, but are not limited to, beta-lactam antibiotics such as subclasses Penicillins (examples: penicillin G, methicillin, oxacillin, ampicillin, amoxicillin), Glycopeptides (example vancomycin), Carbapenems (examples imipenem and meropenem), Polymyxin and Bacitracins (example bacitracin, neomycin) or Lipopeptides (example daptomycin), Protein synthesis inhibitors such as subclasses Aminoglycosides (example gentamicin, streptomycin, kanamycin), Tetracyclines (examples tetracycline, doxycycline, and tigecycline), Oxazilodinone (linezolid), Peptidyl transferases (example Chloramphenicol), Macrolides (examples erythromycin, azithromycin, telithromycin), Lincosamides (examples clindamycin), and Streptogramins (example prisintamycin), DNA synthesis inhibitors such as metronidazole and subclass Fluoroquinolones (examples ciprofloxacin, norfloxacin, morifloxacin), RNA synthesis inhibitors such as rifampin, Mycolic acid synthesis inhibitors such as isoniazid, and Folic acid synthesis inhibitors such as Trimethoprim and subclass Sulfonamides (examples sulfamethoxazole, sulfadoxin). In one embodiment, ALAFAC and the antibiotic in the combination composition are at amounts that will not have bactericidal effect if administered alone. In another embodiment, the ALAFAC is at an amount that will not have a bactericidal effect by itself, and the antibiotic is at an amount that it will have a minimal effect if administered by itself such that it would not be deemed as treatment by a clinician. In another embodiment, the ALAFAC is at an amount that will not have a bactericidal effect by itself, and the antibiotic is at an amount that it will have a therapeutic effect if administered by itself.

In another aspect, the present disclosure provides pharmaceutical compositions. Pharmaceutical compositions comprise, or consist essentially of, ALAFAC with or without the antibiotic, and suitable carriers and other additives. ALA and fatty acids may also be present in the compositions. For example, the composition may comprise a therapeutically effective amount of ALAFAC, and optionally one or more antibiotics, in a pharmaceutically acceptable carrier. Such carriers may include a diluent, adjuvant, excipient, or other vehicle with which the therapeutic is administered. Some examples of materials which can serve as pharmaceutically-acceptable carriers include: sugars, such as lactose, glucose and sucrose; starches, such as corn starch and potato starch; cellulose, including sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The composition, if desired, can also contain minor amounts of wetting or emulsifying agents, or pH buffering agents. Some examples of compositions suitable for mixing with the agent can be found in: Remington: The Science and Practice of Pharmacy (2005) 21st Edition, Philadelphia, Pa. Lippincott Williams & Wilkins. In one embodiment, the agent is substantially purified (e.g., substantially free from substances that limit its effect or produce undesired side-effects).

In one embodiment, the compositions are formulated for topical, transdermal, or mucosal use. Dosage forms for the topical, transdermal or mucosal administration include powders, sprays, ointments, pastes, creams, lotions, gels, solutions, patches and inhalants. The components of the present disclosure may be mixed under sterile conditions with a pharmaceutically-acceptable carrier, and with any preservatives, buffers, or propellants which may be required. The ointments, pastes, creams and gels may contain additional excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Topical powders and sprays can also contain additional excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane. In one embodiment, transdermal patches may be used. These have the added advantage of providing controlled delivery to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel. In one embodiment, the compositions are applied to dermal patches, bandages, gauges or other similar materials that can be directly applied to the affected area.

In one embodiment, the composition may be administered as an aerosol. This can be accomplished by preparing an aqueous aerosol, liposomal preparation or solid particles containing the active agents. A non-aqueous (e.g., fluorocarbon propellant) suspension could also be used. An aqueous aerosol may be made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), sorbitan esters, oleic acid, lecithin, such as glycine, buffers, salts, sugars or sugar alcohols. Aerosols generally are prepared from isotonic solutions. Sonic nebulizers may be used so as to minimize exposing the agent to shear, which can result in degradation of the compound.

In one embodiment, the composition may be formulated for parenteral, intravenous, or intramuscular delivery. These are typically aqueous compositions. Saline solutions and aqueous dextrose and glycerol solutions can also be employed as liquid carriers.

The compositions are administered in a therapeutically effect amount. It will be recognized by those of skill in the art that the form and character of the particular dosing regimen for the therapeutic agent of the present invention will be dictated at least in part by the route of administration and other well-known variables, taking into account such factors as the size, gender, health and age of the individual to be treated, and risk factors associated with cancer development for the individual, such as occupational, behavioral or family history related parameters. Based on such criteria, one skilled in the art can determine an effective amount of to administer to the individual.

The compositions may be delivered by any route. For example, the compositions may be delivered as topical formulation for application to mucosal surfaces. In one embodiment, the compositions may be delivered by routes other than topical or mucosal. For example, the compositions may be delivered via the digestive tract (as oral formulations) or via the circulatory system (intravenous, intramuscular, etc.) or directly to the relevant site.

While not intending to be bound by any particular theory, we provide data, which elucidates the mechanism by which ALAFAC might carry out its potentiation activity. *S. pneumoniae* was the most ALAFAC-sensitive bacterial species tested and showed a minimal inhibitory concentration (MIC) for ALAFAC of ≈20 μg/ml in liquid culture, comparable to the MIC of gentamicin of 16 μg/ml. For time-kill assays, considerably higher concentrations were needed (300 μg/ml to eradicate an inoculum of $10^8$ pneumococci in 1 hour). These numbers are also comparable to what is required to kill pneumococci with other antibiotics in the same time frame and may be within a physiological range considering that the concentration of ALA in milk is high (2,000 μg/ml). ALAFAC kills all pneumococcal antibiotic-resistant strains that were tested (penicillin, erythromycin, tetracycline, and chloramphenicol-resistant), suggesting that ALAFAC works through a pathway different from common antibiotics. Using *S. pneumoniae* as a model organism, we show that ALAFAC causes dissipation of the proton motive force, an influx of calcium through a sodium dependent mechanism and activation of serine/threonine kinase activity and leads to depolarization of the bacterial membrane. Furthermore, attempts to produce spontaneous mutants resistant to ALAFAC or mutants becoming resistant after slow adaptation to increasing concentrations of ALAFAC were unsuccessful. This suggests either that components being activated are essential for the bacteria or cannot be inactivated merely with point-mutations, or that there are multiple compensating pathways activated by ALAFAC.

One embodiment of the present disclosure is aimed as an adjuvant to current antibiotic use to lower the concentrations of antibiotics needed to kill various bacterial species. One application for this disclosure is to lower the concentration of antibiotics needed to treat and eradicate resistant bacterial species to increase treatment efficacy and to enable the prolonged the use of the same antibiotic in the clinic. In various embodiments, a 2 to 300 fold reduction is observed in the MIC for bacteria by using a combination of antibiotic and ALAFAC compared to the antibiotic alone. Also, by lowering the concentration of antibiotics used in general, ALAFAC adjuvant therapy has the potential to produce less side effects as ALAFAC by itself is a natural molecule ingested by infants, and importantly, produce less risk for further resistance development.

In one embodiment, human alpha-lactalbumin in complex with a C16 or C18 fatty acids can sensitize antibiotic-sensitive, and/or antibiotic-resistant strains of various species of bacteria (including, but not confined to, *Streptococcus pneumoniae, Staphylococcus aureus, Acenitobacter baumanii, Moraxella catarrhalis*, and *Haemophilus influenzae*) to various classes of antibiotics. In this way combination treatment with ALAFAC and antibiotics may at least (1) lower the clinically useful concentrations of antibiotics used and lower antibiotic use (2) prolong the usefulness of the current treatment arsenal against bacterial infection by sensitizing antibiotic-resistant strains to those same antibiotics, and (3) to use current antibiotics to treat currently untreatable infections.

The features of the disclosure can be used in combination treatments with various classes of traditional antibiotics both to treat infections with antibiotic sensitive strains (skin infections, pneumonia, ear infections etc), thus enabling a lowering of the dose to minimize side effects but also to enable the treatment of infections caused by antibiotic-resistant bacteria (such as MRSA and VRE) using the same antibiotics these bacteria are resistant to and thus increase the usefulness of the current treatment arsenal.

ALAFAC-potentiation of traditional antibiotics may have the advantage of at least (1) enabling the use of a lower dose of antibiotics, thus causing a lower risk for further antibiotic resistance, (2) causing higher levels of sensitization, to several antibiotic classes in many different bacterial species and (3) as we were unable to induce ALAFAC resistance in the laboratory, the use of ALAFAC is expected to be safer and not be easily inactivated in a clinical setting.

In another aspect, the present disclosure provides methods for using the compositions. The method comprises the steps of administering to an individual (human subject or another non-human subject), a composition comprising or consisting essentially of, in separate or same formulation, ALAFAC or its components, and one or more antibiotics, wherein the activity of the antibiotic is potentiated upon administration of ALAFAC or its components. In one embodiment, the disclosure provides a method for inhibiting the growth of bacteria. In one embodiment, the method comprises the steps of providing a combination of ALAFAC and an antibiotic and delivering the ALAFAC and the antibiotic to the bacteria, wherein the growth of the bacteria is inhibited. The combination of ALAFAC and the antibiotic may be delivered in the form of a single composition or separate compositions. The bacteria may be contacted with the combination at the site of growth of bacteria. This site may be outside of a living system or may be inside a living system (as in the case of an infection).

In one embodiment the present disclosure provides a method for potentiating the activity of antibiotics by administering to an individual the antibiotic prior to, concomitantly with, or after the administration of ALAFAC. The ALAFAC may be administered at amounts that may have only an adjuvant effect, or an adjuvant effect as well as a bactericidal effect. The potentiation of antibiotic activity may be achieved in bacteria that are sensitive to the antibiotic or in bacteria that are resistant to the antibiotic. The individual may be any mammal including, but not limited to, humans, cattle, dogs, horses, and the like. In one embodiment, the individual is a human subject. In one embodiment, the individual is a human subject who is diagnosed as having, is suspected of having, or is at risk of having a bacterial infection. In one embodiment, the human subject is diagnosed as having, is suspected of having, or is at risk of having an antibiotic resistant infection. In one embodiment, the human subject is diagnosed as having, is suspected of having, or is at risk of having a MRSA infection.

In one embodiment, the present disclosure provides a method of treatment of infections, including but not limited to, infections of the skin and mucosal surfaces (gastrointestinal tract, respiratory tract etc.), internal infections, sepsis and the like. In one embodiment, the present disclosure provides a method of treatment of wound infections. In one embodiment, the wound infection is caused by methicillin resistant *Staphylococcus aureus*. The method comprises administration to the individual ALAFAC and an antibiotic. In one embodiment, the ALAFAC is delivered as a topical formulation to the site of the wound. The antibiotic may be delivered in the same formulation as ALAFAC, in a different formulation to the same site, or may be delivered as a different formulation to a different site or via a different mode (such as systemically). In one embodiment, the antibiotic is penicillin, oxacillin, vancomycin, erythromycin and the like.

In one embodiment, the present disclosure provides a method for reducing colonization, which frequently accompanies wound infections, particularly MRSA infections. Colonization is generally found on the skin and mucosal surfaces and particularly in the nasal area. The nasal colonization is often considered to be responsible for repeat infections. Thus, in one embodiment, the method comprises administering to the non-wound region (such as the non-wound area of the skin, and other mucosal surfaces such as the nares), a formulation (such as a mucosal formulation) comprising ALAFAC and an antibiotic. The ALAFAC and the antibiotic may be delivered together or separately.

In one embodiment, both a wound infection and extra-wound colonization can be reduced and/or treated by administering to an individual a combination of ALAFAC (delivered at the wound) and an antibiotic, and also delivering to the expected colonization area, the combination of ALAFAC and the antibiotic. If the colonization is in the nares, a spray formulation or other formulations that can deliver the ALAFAC and the antibiotic to the nares, either together or separately, can be used.

This disclosure also provides a method for treating a bacterial infection that has become resistant to antibiotic treatment. Determination of whether a bacterial infection is resistant to a particular antibiotic may be from clinical observations after administration of the antibiotic, or may be made by culturing the bacteria from the individual and testing the bacteria for sensitivity to various antibiotics. A combination of ALAFAC and the antibiotic to which the infection has become resistant is administered, either separately or together, either via same routes or different routes, either simultaneously or at different times.

In one embodiment, the present disclosure provides a method for treatment of gastrointestinal tract infections by administering to an individual suffering from the infection an oral formulation of ALAFAC, and the antibiotic. In one embodiment, the oral formulation may comprise ALA and fatty acids instead of, or in addition to, ALAFAC, such that the ALA and fatty acids may combine in vitro or in vivo to form ALAFAC. The antibiotic may be delivered orally, or via other routes (such as intravenous).

In one embodiment, the present disclosure provides a method for treatment of respiratory tract infections by administering to an individual suffering from the infection a formulation suitable for delivery to the respiratory tract (such as via an pump inhaler or pressurized inhaler etc.).

In one aspect, the present disclosure provides kits useful for treatment of infections. In one embodiment, the kit comprises a treatment set, wherein the treatment set includes a) one or more containers, each container containing ALAFAC, optionally in a pharmaceutically acceptable carrier, said treatment set being in an amount such that it would not be effective for killing bacteria by itself, but would be effective as an adjuvant for potentiating the effect of an antibiotic; and b) directions for use of said treatment set. The directions may indicate which antibiotic the treatment set is suitable for use with (such as, for example, MRSA, *S. pneumoniae* etc.), and/or the type of infections it can be used for (such as, for example, skin, mucosal surfaces, respiratory tract, gastrointestinal tract, ears, and the like). The directions may also include the administration details and regimen. The dose or portion in each container may be in the form of a liquid, powder, pressed materials such as tablets, sequestered materials such as geltabs and the like. In one embodiment, instead of a container containing ALAFAC, there may be multiple containers whose contents may be combined to form ALAFAC. For example, there may be separate containers containing ALA, fatty acids, and suitable buffer. The contents of these containers can be combined to form ALAFAC. In this instance, the directions with the treatment set may also comprise directions for combining the ALA and the fatty acids to form the complex. The directions may also direct a user to administer the ALA and fatty acids to an individual such that ALAFAC may form in vivo or in vitro.

Figures 5A, 5B, 5C:
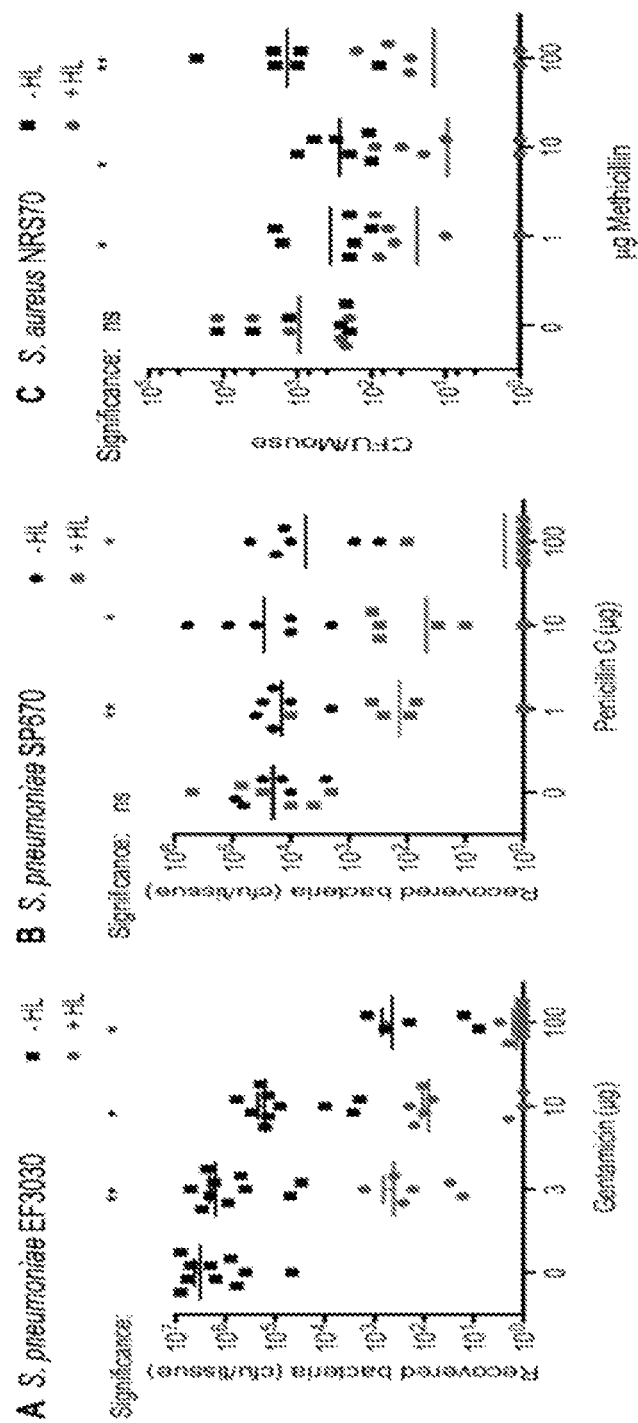
FIGS. 5A, 5B, and 5C are charts illustrating that antibiotic combination treatment eradicates pneumococci and MRSA during nasopharyngeal colonization. (A) Mice were colonized with the penicillin-sensitive *S. pneumoniae* EF3030 strain for 48 hours, treated intranasally with various doses of gentamicin in the presence (circles) or absence (squares) of ALAFAC (labeled as HL) (50 μg) for 6 hours, and the bacterial burden associated with the nasopharyngeal tissue was determined (B) Mice were colonized with the penicillin-resistant strain S. pneumoniae SP670 (MIC=4 μg/mL) for 48 hours, treated intranasally with various doses of penicillin in the presence (squares) or absence (circles) of ALAFAC (50 μg) for 12 hours and the bacterial burden associated with the nasopharyngeal tissue was determined. Penicillin alone had no effect on the bacterial burden. (C) Mice were colonized with the methicillin-resistant strain S. aureus NRS70 for 48 hours, treated intranasally with various doses of methicillin in the presence (circles) or absence (squares) of ALAFAC (50 μg) for 12 hours and the bacterial burden associated with the nasopharyngeal tissue was determined. Methicillin alone had no effect on the bacterial burden. The graph shows colonization data for individual mice, with the mean recovered bacteria and the standard deviation depicted. The results are based on experiments using groups of 6-10 mice. Statistics was performed using the unpaired Student t-test. Significance was indicated as follows: *=P<0.05, **=P<0.01, ns=non-significant.

In another embodiment, the treatment set comprises a container comprising ALAFAC and an antibiotic. In one embodiment, the amount of antibiotic and the ALAFAC represents one or multiple doses of the combination that is to be administered. In one embodiment, the amount of antibiotic that represents a dose is less than the dose that is normally used for treating of infections. For example, as shown in FIG. 5A, a 30 fold lower dose was required when the antibiotic was used with ALAFAC against *S. pneumoniae* EF3030. In another embodiment, the treatment set has separate containers for ALAFAC and the antibiotic, or ALAFAC components (ALA and fatty acids) and the antibiotic.

In one embodiment, the amount of antibiotic that represents a dose is from 2 to 100 times or 2 to 10 times less than the normal dose used for treating infections. In one embodiment, the dose is at least 2 times less than the dose used to normally treat infections.

In various embodiments, the present disclosure provides the following: a composition suitable for administration to an individual comprising: i) alpha lactalbumin fatty acid complex, wherein the fatty acids in the complex comprise cis, unsaturated C14, C16, C18 and/or C20 fatty acids; and ii) an antibiotic, the alpha-lactalbumin fatty acid complex and the antibiotic being present in a pharmaceutical carrier, wherein i) potentiates the action of the antibiotic for treatment of an infection in the individual. The individual may be a human subject or a non-human subject.

A method of potentiating the effect of an antibiotic and/or for treating a bacterial infection in an individual comprising the steps of: a) providing a composition comprising alpha lactalbumin complexed to fatty acids, wherein the fatty acids comprise cis, unsaturated C14, C16, C18 and/or C20 fatty acids; b) administering to an individual the composition from a); and c) separately, or together with b), administering an antibiotic to the individual, wherein the alpha lactalbumin complexed to fatty acid(s) potentiates the action of the antibiotic for treatment of an infection in the individual. The individual may be a human subject or a non-human subject.

A kit for treatment of infections comprising: a) alpha lactalbumin fatty acid complex in an amount suitable to potentiate the antibacterial activity of an antibiotic; b) the antibiotic in an amount suitable to treat the infection in the presence of a); c) instructions for administration of a) and b), wherein a) and b) are administered separately or together via same or different routes. The kit may be in the form of a single use package or multiple use packages. The formulations a) and b) may be present in the same compositions or in separate compositions. The kit may also indicate whether it is for human or veterinary use.

A kit for potentiating the effect of an antibiotic comprising: a) a treatment set comprising one or more containers, each container comprising a formulation comprising alpha lactalbumin fatty acid complex, wherein the amount of alpha-lactalbumin fatty acid complex in the treatment set is sufficient for potentiating the effect of an antibiotic; and b) directions for use of a), wherein the directions include one or more of the following: i) an indication of the antibiotic whose effect a) will potentiate, ii) an indication of the infection that can be treated with the combination of a) and an antibiotic; and iii) an indication of administration details. For example, the instructions may indicate that the kit is suitable for use in treatment of MRSA infections and/or may indicate useful antibiotics for use with the ALAFAC for the treatment of MRSA. Similarly, the kit may indicate that it is suitable for the treatment of respiratory infections, gastrointestinal infections, ear infections, sepsis or any other infection, and may indicate the antibiotic(s) for use with the ALAFAC for the treatment of the infections. This kit may also comprise one or more containers containing the antibiotic. The formulation from each container may be used for single or multiple applications. The kit may also indicate whether it is for human or veterinary use.

The following examples are presented to illustrate the present disclosure. They are not intended to limiting in any manner.

Example 1

Figure 1:
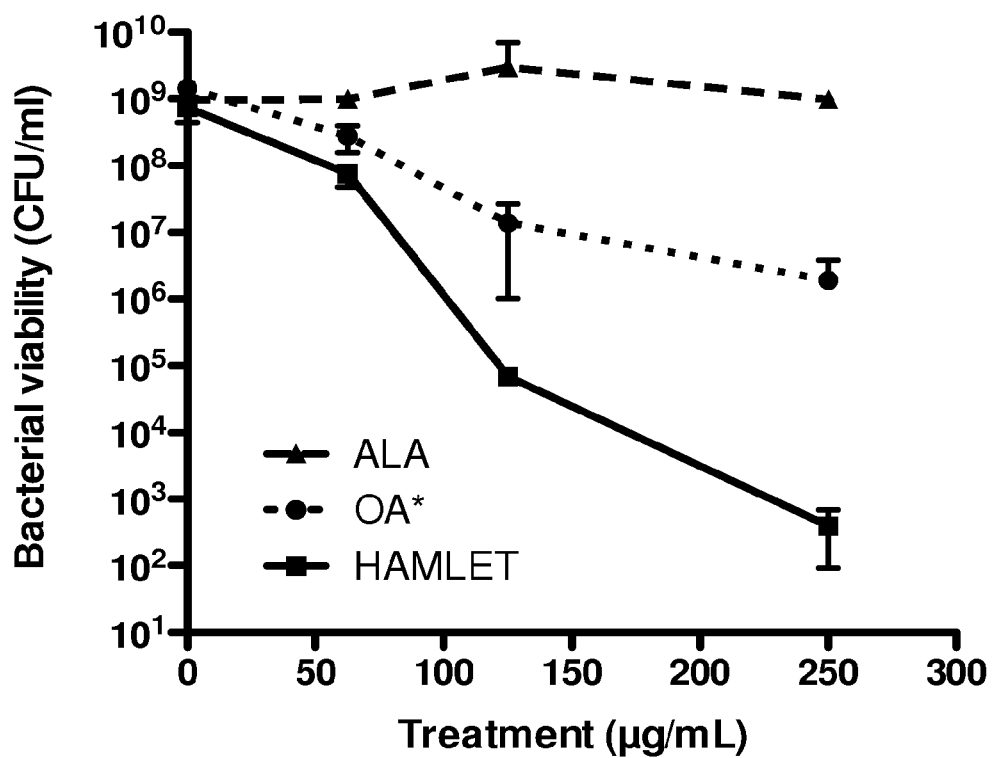
FIG. 1 is a chart showing *S. pneumoniae* D39 treated with native alpha-lactalbumin (ALA), ALAFAC, or oleic acid (OA) at the concentration equivalent to the concentration present in ALAFAC (6% w/w) and incubated for 1 hour at 37° C. Viable organisms were assessed after plating dilutions of each sample onto blood agar plates and enumerating colony forming units after overnight growth.

This example illustrates the adjuvant activity of ALAFAC. For initial purifications, milk was separated into the whey and casein fractions, with the bactericidal activity following the casein fraction and was purified further using ion-exchange and size exclusion chromatography. The final bactericidal fraction was analyzed for protein content and was found to contain alpha-lactalbumin (ALA) as the only identifiable protein. ALA is the most common protein in human milk (approx. 2 g/l concentration). In its native form, human ALA (a whey protein) had no bactericidal activity (FIG. 1, dashed line), suggesting that the bactericidal version of alpha-lactalbumin was changed in some respect. Although both oleic acid and linoleic acid have bactericidal activity by themselves, the concentrations required to kill bacteria are considerably higher (FIG. 1, dotted line) than the concentrations associated with the ALAFAC-complex (FIG. 1, solid line. It was observed that fatty acids were necessary for bactericidal activity, no activity is observed unless lipid is attached. Also, human ALA can be exchanged for bovine, equine, porcine and caprine ALA (75-79% sequence identity). This experiment was done on *S. pneumonia*.

ALAFAC and common antibiotics were tested to determine whether ALAFAC and common antibiotics could synergize to kill pneumococci in vitro and in vivo. The results were unexpectedly promising, which led to an investigation of ALAFAC's synergistic effects with bacterial species ALAFAC alone cannot kill.

Methodology: Minimal inhibitory concentrations (MICs) were determined in 96-well microtiter plates using the microdilution method according to approved standards of the CLSI except that Todd-Hewitt medium supplemented with 0.5% yeast extract, which yields reproducible MIC results was used as the test medium for *S. pneumoniae*. For the remaining species Mueller-Hinton medium was used as indicated by the CLSI standard. Each well contained twofold dilutions of antibiotic, was seeded with a final bacterial concentration of $10^5$ CFU/mL, and was incubated for 18 h at 37° C. in a Synergy II microplate reader (Biotek, Winooski, Vt.) where the $OD_{600}$ was recorded every 5 minutes to monitor bacterial growth. The MIC was defined as the lowest concentration of antimicrobial agent solution at which no increase in $OD_{600}$ was detected.

Figures 2A, 2B:
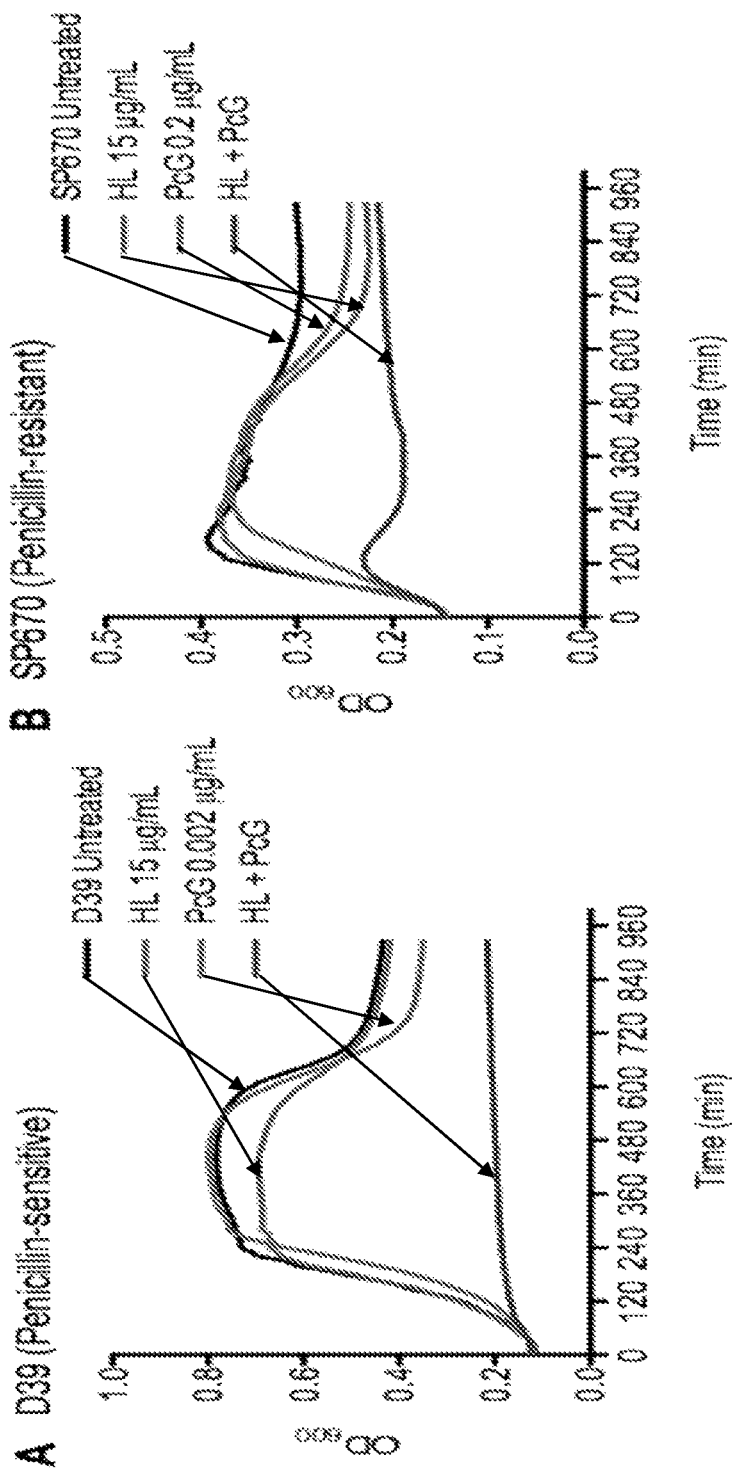
FIGS. 2A and 2B are charts showing ALAFAC (labeled as HL) lowering the MICs of penicillin G. The penicillin-sensitive *S. pneumoniae* strain D39 (A) and the penicillin-resistant strain SP670 (B) were grown in broth for 16 hours in the presence of penicillin G with and without the addition of ALAFAC. The figures show representative growth curves for the lowest concentration of antibiotic and ALAFAC that inhibited bacterial growth by combination treatment without either agent alone affecting growth.

FIG. 2 shows the results when the MIC was measured using penicillin G as an antibiotic, but similar results are obtained with erythromycin and gentamicin, which represent two separate classes of antibiotics (macrolide and aminoglycoside, respectively; Table 1). For penicillin, co-treatment with ALAFAC reduces the minimal inhibitory concentration of a penicillin-sensitive strain 5-fold (FIG. 2A) and shows an even greater, over 20-fold, reduction of the MIC in penicillin-resistant strains (FIG. 2B). This reduction in MIC makes the penicillin-resistant strain reach the penicillin-sensitive range.

The same pattern was true for the macrolide erythromycin. In the absence of ALAFAC, the MIC of erythromycin for the sensitive strain D39 was 0.03 µg/mL and for the D39-derived, erythromycin-resistant strain JY53, carrying an erythromycin resistance cassette in the PspA locus, was 100-fold higher at 3 µg/ml (Table 1). In the presence of 0.75×MIC of ALAFAC the MIC of erythromycin was reduced 3-fold to 0.01 µg/ml in the sensitive strain and significantly more (300-fold; P<0.001) to 0.01 µg/ml in the resistant strain, making this strain highly susceptible to this antibiotics and equally sensitive as the non-resistant D39 strain in the presence of ALAFAC (Table 1).

Finally, the MIC of the aminoglycoside gentamicin was 16 µg/mL for both *S. pneumoniae* D39 and EF3030. In the presence of 0.75×MIC of ALAFAC the MIC of gentamicin was reduced 4-fold, to 4 µg/mL in both strains (Table 1).

Although ALAFAC does not, by itself, kill bacterial species such as Staphylococci and *E. coli*, it was observed that depolarization of the membrane and ion transport occurred in both species although not to a degree that triggered death even at concentrations exceeding 1,000 µg/ml. Therefore it was tested whether this effect may help in lowering the MIC of other antibiotics. As seen in Table 1, strains of the emerging pathogen *Acinetobacter baumanni*, *Moraxella cartarrhalis*, *Staphylococcus aureus*, three species with high resistance to various antibiotics could all be shown to reduce their MICs for penicillin, erythromycin, gentamicin, vancomycin and methicillin between 4 and 160-fold. Of major interest, was the fact that strains of *Moraxella* that are inherently and highly penicillin-resistant could become penicillin intermediately sensitive in the presence of ALAFAC and that ALAFAC could make methicillin-resistant *S. aureus* (MRSA) strains sensitive to methicillin.

Short-time kill assays: To further analyze whether the effect seen in the MIC assays were due to a bacteriostatic or a bacteriolytic effect, a short time kill assays with antibiotics alone or in combination with ALAFAC was performed.

Methodology: In late logarithmic growth phase, the bacteria were harvested by centrifugation at 12,000×g for 10 minutes and resuspended in phosphate-buffered saline (PBS; 30 min $Na_2HPO_4$, 10 min $KH_2PO_4$, 120 min NaCl, pH 7.4). Appropriate dilutions of the bacteria were suspended in PBS and treated with indicated concentrations of ALAFAC and/ or antibiotics for various times. The effect on bacterial viability was assessed by plating serial dilutions of bacterial sample on tryptic soy agar plates containing 5% sheep blood (viable counts) and determining viable colony forming units after overnight growth at 37° C. Bactericidal activity was defined as the reduction of a least 3 $\log_{10}$ CFU.

Results: Starting with *S. pneumoniae*, for each of these experiments, ALAFAC and each antibiotic were titrated to produce a bactericidal activity of less than 1 $\log_{10}$ in sensitive strains, respectively, over the incubation time and those concentrations were then used to perform combination treatments.

Figures 3A, 3B:
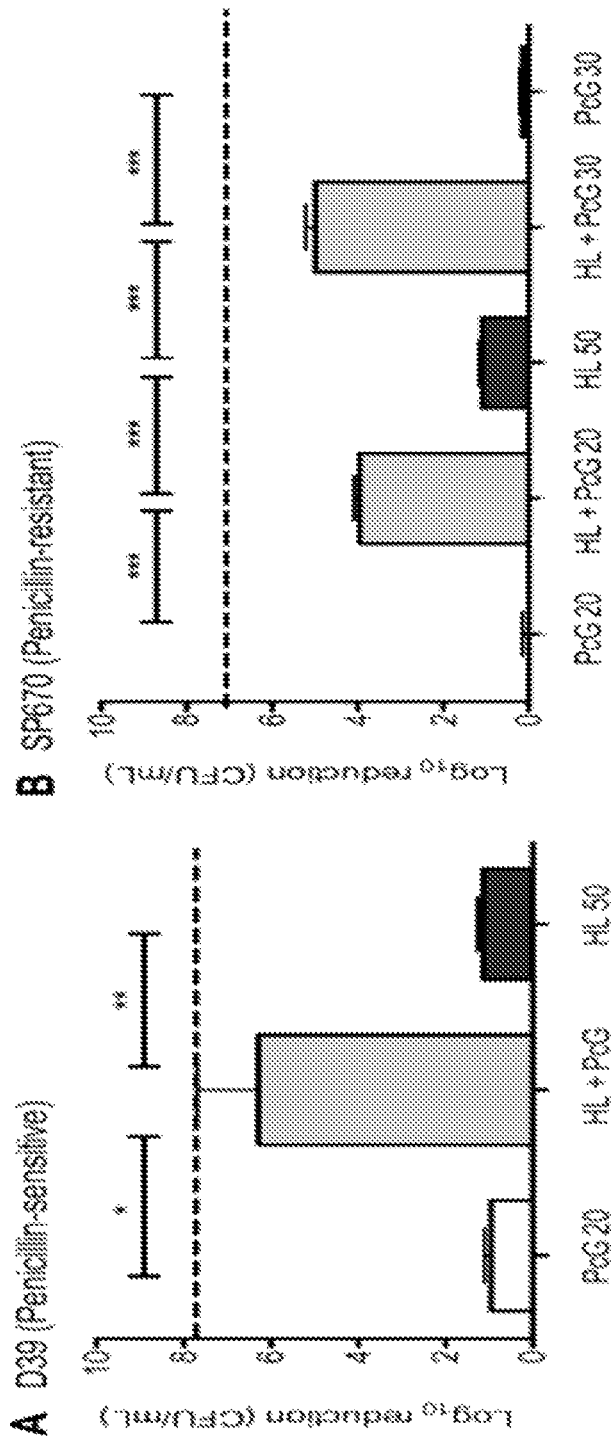
FIGS. 3A and 3B are charts showing potentiation of short-time pneumococcal killing by penicillin in the presence of ALAFAC (labeled as HL). Short-time killing of the penicillin-sensitive strain D39 (A) by penicillin (20 µg/mL), ALAFAC (50 µg/mL) and penicillin combined with ALAFAC over 4 hours. (B) Killing of the penicillin-resistant strain SP670 by penicillin (20 or 30 µg/mL), ALAFAC (50 µg/mL), or penicillin combined with ALAFAC over 4 hours. The dashed horizontal line represents the total bacterial inoculum of an untreated sample. The results are based on three individual experiments with duplicate samples and are expressed as means±S.D. Statistics was performed using the unpaired Student t-test. Significance was indicated as follows: *=P<0.05, =P<0.01, *=P<0.001, ns=not significant.

For penicillin G, the most successful combination effect was seen using 50 µg/ml of ALAFAC and 20 µg/ml of penicillin G that alone caused less than 1 $\log_{10}$ or no death of D39 pneumococci, respectively, over 4 hours, the amount of time needed to obtain bactericidal activity of this bacteriostatic antibiotic. However, combination treatment of the two agents resulted in significantly higher killing than the added killing of each agent alone (P<0.05) with near eradication of the 7.5 $\log_{10}$ bacterial inoculum (FIG. 3A). To obtain a similar activity with ALAFAC alone, more that 5-fold higher concentrations were required, and penicillin G failed to kill more than 2.6 $\log_{10}$ by itself, even at a 250-fold higher concentration (5,000 µg/ml) for 4 hours. The potentiation effect was also present in the penicillin-resistant strain SP670 that had a 20-fold higher MIC than the D39 strain. Combination treatment with 50 µg/mL ALAFAC and 20 µg/mL penicillin G killed 4.0 $\log_{10}$ of the 7.6 $\log_{10}$ inoculum, which was significantly higher than either agent alone or the additive effect of the two agents (P<0.001; FIG. 3B). Increasing the penicillin concentration to 30 µg/mL (that had no bactericidal activity by itself) resulted in killing of 5.0 $\log_{10}$ when combined with ALAFAC, which was also significantly higher than the added killing of each agent alone (P<0.001; FIG. 3B).

Similar and even stronger effects were seen when a sublethal concentration of ALAFAC was combined with erythromycin. 50 µg/ml of ALAFAC and 200 µg/ml of erythromycin showed insignificant bactericidal activity by themselves against the sensitive strain D39, whereas the combination of the two agents resulted in significantly increased killing than the added killing of each agent alone (P<0.001) with near-eradication of the 7.2 $\log_{10}$ inoculum (Table 2). When using the erythromycin-resistant strain JY53 that displayed a 100-fold higher MIC, combination of the two agents at the same concentrations (200 µg/mL erythromycin together with 50 µg/mL ALAFAC) caused 4.1 $\log_{10}$ of pneumococcal death after 4 hours (P<0.05 compared with the added killing of each agent alone), which could be increased to complete eradication of the bacterial inoculum when 300 µg/mL erythromycin (P<0.001 compared with the added killing of each agent alone) was used together with 50 µg/mL ALAFAC, a highly significant potentiation in killing of erythromycin-resistant pneumococci (Table 2).

Finally, using 50 µg/ml of ALAFAC or 50 µg/ml of the aminoglycoside gentamicin alone caused insignificant killing of D39 pneumococci, whereas combining the two agents resulted in a significantly enhanced bactericidal activity compared with the added killing of the two agents (P<0.001) with the entire bacterial inoculum (7.7 $\log_{10}$) eradicated after only 1 hour of incubation. This was substantial as gentamicin was unable to kill more than 1.4 $\log_{10}$ by itself, even at concentrations up to 1,000 µg/ml.

The results with *S. pneumoniae* were confirmed with the *S. aureus* strains where a 10-fold reduction in concentration of gentamicin obtained eradication of the *S. aureus* inoculum in the presence of ALAFAC (Table 2). Similar >2-32 fold decreases in methicillin were obtained in the presence of ALAFAC, depending on strains, with the most resistant strains showing most change in sensitivity, similar to the MIC values above.

These results suggest that ALAFAC acts as a powerful bactericidal potentiator of several classes of antibiotics and is able to significantly decrease the antibiotic concentrations needed to induce death of pneumococci.

Biofilm assays in vitro: As all the organisms tested above colonize and infect in the body in bacterial communities or biofilms that further increases their antibiotic resistance, verifying that the synergistic effects seen were also valid against bacteria grown in biofilm format was of interest. Pneumococci colonizing or infecting the mucosal surfaces of the host grows primarily in aggregated communities or biofilms are known to display substantially increased resistance to antibiotics as well as other antimicrobial agents.

Methodology: Pneumococci were grown statically in CDM and *S. aureus* were grown in trypic soy medium to mid-logarithmic phase ($OD_{600}$=0.5), washed, and resuspended in fresh pre-warmed medium to a density of $2 \times 10^4$ CFU in 500 µl volume, and suspensions were used to seed sterile round glass coverslips in the bottom of polystyrene 24-well plates with or without a substratum of confluent H292 epithelial cells. Biofilms were cultured at 34° C. in 5% $CO_2$ for indicated times with change of culture media every 12 hours and to assess biomass and antibiotic resistance by viable counts (as described).

Pre-formed biofilms were washed with PBS to eliminate planktonic bacteria and were exposed to PBS with indicated concentrations of ALAFAC and/or antibiotics for 3 hours at 34° C. in 5% $CO_2$. Biofilms were then washed in PBS and detached by scraping the surface in the presence of 100 µL PBS followed by a rinse with 100 µL PBS. Collected cells were sonicated in a sonication water bath for 2 s followed by vortexing twice for 20 seconds at high speed and the dispersed biofilm cells were used to determine viable CFUs per ml from diluted samples plated and grown on blood agar. Results are reported as the total number of colony-forming units per biofilm and the bactericidal activity was defined as the reduction of a least 3 $\log_{10}$ CFU.

Figures 4A, 4B:
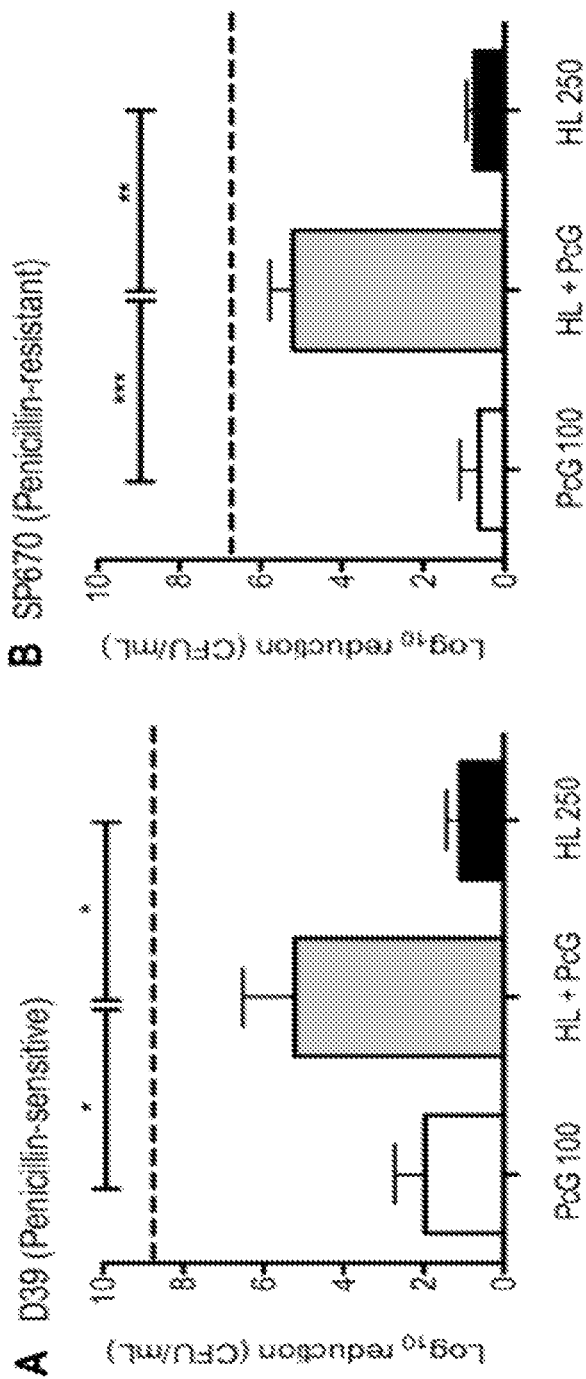
FIGS. 4A and 4B are charts showing the effect of ALAFAC (labeled as HL)/antibiotic combination treatment on in vitro biofilm viability. The activity of penicillin G (100 µg/mL), ALAFAC (250 µg/mL), or the combination of both agents were tested on in vitro biofilms of the penicillin-sensitive strain D39 (A) or the penicillin-resistant strain SP670 (B) formed over a prefixed epithelium of NCI-H292 cells and were tested by determining the bacterial death (in $log_{10}$) after culturing bacterial dilutions overnight on blood agar. The dashed horizontal line represents the mean total bacterial biomass of biofilms that were treated with buffer alone. The results are based on three individual experiments with duplicate samples. Statistics was performed using the paired Student t-test. Significance was indicated as follows: *=P<0.05, =P<0.01, *=P<0.001.

Results: Bacteria grown as biofilms over epithelial cells has a greatly increased resistance to both ALAFAC and antibiotics, resulting in limited death at high concentrations, but for both the penicillin sensitive pneumococcal strain D39 (FIG. 4A) and the resistant strain SP670 (FIG. 4B) ALAFAC/penicillin combination treatment resulted in eradication of the biofilm (FIG. 4AB, middle bar) with a more than 50 fold reduction in penicillin G concentration used to produce a bactericidal effect (Table 3). Even more pronounced results were seen for erythromycin, although those results do not show in terms of fold numbers based on us not testing monotherapy beyond 1,000 µg/ml (Table 3). The combination of erythromycin with 250 µg/ml ALAFAC resulted in a synergistic increase in anti-biofilm activity with the near eradication (8.5 $\log_{10}$ out of 8.7 $\log_{10}$ killed) of the biofilm after combination treatment, which was significantly higher than the additive effect of each agent (P<0.05). The effect on the erythromycin-resistant strain JY53 was less pronounced, resulting in eradication of 4.3 $\log_{10}$ CFU after treatment with 500 µg/mL erythromycin in combination with 250 µg/ml ALAFAC.

Pneumococcal biofilms formed with EF3030 pneumococci for 48 hours were treated with 100 µg/mL ALAFAC and 200 µg/ml gentamicin alone or in combination for 3 hours. Gentamicin treatment alone killed 1.1 of the total EF3030 biofilm biomass (7.5 log), whereas 100 µg/mL ALAFAC alone had no bactericidal activity. In contrast, the combined treatment of the biofilms with both agents for 3 hours significantly increased the killing to 3.8 logs, which was both significantly higher than the additive effect of each agent (P<0.05) and resulted in a three-fold reduction in gentamicin concentration used to induce a bactericidal activity.

Finally, biofilms formed by one strain of methicillin-sensitive *S. aureus* (MSSA; 11090306) and one strain of methicillin-resistant *S. aureus* (MRSA; NRS70) were insensitive to methicillin up to a concentration of 1,000 µg/ml that only resulted in 1 $\log_{10}$ and 0.16 $\log_{10}$ death, respectively in monotherapy. However in combination with 100 µg/ml ALAFAC that resulted in no death per se, the combination treatment resulted in 4.8 and 3.4 $\log_{10}$ reduction in biofilm biomass, respectively for the MSSA and the MRSA strains (Table 3), producing an at least 4-fold reduction in methicillin concentration required for a bactericidal activity.

In vivo treatment assays: The combination treatment efficacy was determined for colonization of *S. pneumoniae* and *S. aureus* in a murine colonization model known to produce biofilms in vivo.

Methodology: Six-week-old female BALB/cByJ mice from Jackson Laboratories (Bar Harbor, Me., U.S.A.) were maintained in filter-top cages on standard laboratory chow and water ad libitum until use. Mice were colonized as described previously. In short, 20 µl of a bacterial suspension containing 5×10$^6$ CFUs of EF3030 pneumococci, 1×10$^8$ CFUs of SP670 pneumococci, or 5×10$^7$ NRS70 methicillin-resistant *S. aureus* in PBS were pipetted into the nares of non-anesthetized mice. After 48 hours, mice were treated with 20 µl gentamicin (0-5,000 µg/mL), 20 µl penicillin (0-5,000 µg/mL), or 20 µl of methicillin (0-5,000 µg/ml) in the presence or absence of 50 or 100 µg ALAFAC in the nares for 6 hours as a single dose. Colonization burden was then assessed after euthanizing the animals by enumerating viable bacteria from harvested nasopharyngeal tissue after the nasal wash. Nasopharyngeal tissue was dissected out as described by removing the upper skull bone, and harvesting the tissue present in the nasal conchae with forceps. Bacterial load was measured by determining viable plate counts from the homogenized tissue.

Results: Mice treated with ALAFAC alone showed no decrease in bacterial burden after stable colonization had been induced for 48 hours using a single dose of 50 µg of ALAFAC. However, the bactericidal antibiotic gentamicin alone caused a slow reduction of the bacterial burden of pneumococci starting at a dose of 10 µg/mouse in the nasopharyngeal tissues. Still, bacteria associated with the tissue were highly resistant to gentamicin and substantial growth was detected even after a dose of 100 µg (5,000 µg/ml), 10 times the killing dose in vitro (FIG. 5A). However in the presence of ALAFAC, a comparable decrease in tissue associated bacterial load was obtained using a 33-fold lower dose (3 µg) of gentamicin (150 µg/ml) (FIG. 5A).

Treatment of nasopharyngeal colonization of the penicillin-resistant strain SP670, with increasing concentrations of penicillin had no effect on the colonization levels, not even when a dose of 100 µg (5,000 µg/ml) was added intranasally. The same was true when ALAFAC alone was added. However, when ALAFAC and penicillin was used together a 100-fold reduction of the bacterial burden was seen already at 1 µg of penicillin (50 µg/ml) and the bacteria were eradicated from the nasopharynx at 100 µg local dose (FIG. 5B).

Similarly, treatment of colonization with the methicillin-resistant *S. aureus* strain NRS70 with methicillin alone had no effect on colonization burden even at a single dose of 100 µg (5,000 µg/ml), which was also true for treatment of ALAFAC at the same dose. However, a significant reduction in colonization was observed when methicillin was treated in combination with ALAFAC with near eradication at a dose of 10 µg. As the colonization rate was rather low, which is usually the case for *S. aureus* in this model system, a true 3 $\log_{10}$ reduction bactericidal efficacy could not be detected. However, significant reduction of bacterial load was observed already at 1 µg of methicillin, 100 times lower than the highest concentration used, which by itself had no activity on bacterial colonization.

TABLE 1

MIC values for various antibiotics in the presence and absence of ALAFAC used at 0.75X MIC (15 µg/mL) for *S. pneumoniae* and at 100 µg/ml for remaining species.

| Bacterial Strain | Antibiotics, MIC (µg/ml) | | Fold reduction |
|---|---|---|---|
| | Penicillin | Penicillin + HL* | |
| D39 (*Streptococcus pneumoniae*) | 0.01 | 0.002 | 5 |
| SP670 (*Streptococcus pneumoniae*) | 4 | 0.2 | 20 |
| AB307 (*Acinetobacter baumanni*) | >100 | 25 | >4 |
| AB979 (*Acinetobacter baumanni*) | >100 | 25 | >4 |
| MC7169 (*Moraxella catarrhalis*) | >50 | 1.56 | >32 |
| MCBC8 (*Moraxella catarrhalis*) | >50 | 12.5 | >4 |

TABLE 1-continued

MIC values for various antibiotics in the presence and absence of
ALAFAC used at 0.75X MIC (15 μg/mL) for *S. pneumoniae*
and at 100 μg/ml for remaining species.

| Bacterial Strain | Antibiotics, MIC (μg/ml) | | Fold reduction |
|---|---|---|---|
| | Erythromycin | Erythromycin + HL* | |
| D39 (*Streptococcus pneumoniae*) | 0.03 | 0.01 | 3 |
| JY53 (*Streptococcus pneumoniae*) | 3 | 0.01 | 300 |
| NRS384 (*Staphylococcus aureus*) | 16 | 4 | 4 |
| | Gentamicin | Gentamicin + HL* | |
| D39 (*Streptococcus pneumoniae*) | 16 | 4 | 4 |
| EF3030 (*Streptococcus pneumoniae*) | 16 | 4 | 4 |
| AB307 (*Acinetobacter baumanni*) | 36 | 4.5 | 8 |
| AB979 (*Acinetobacter baumanni*) | 2.5 | 1.25 | 2 |
| MC7169 (*Moraxella catarrhalis*) | 25 | 6.7 | 4 |
| MCBC8 (*Moraxella catarrhalis*) | 25 | 6.7 | 4 |
| NRS384 (*Staphylococcus aureus*) | 1 | 0.00625 | 160 |
| | Vancomycin | Vancomycin + HL* | |
| NRS384 (*Staphylococcus aureus*) | 1 | 0.5 | 2 |
| NRS1 (*Staphylococcus aureus*) | 8 | 4 | 2 |
| | Methicillin | Methicillin + HL* | |
| NRS1 (*Staphylococcus aureus*) | >128 | 16 | >8 |
| NRS70 (*Staphylococcus aureus*) | 32 | 1 | 32 |
| NRS71 (*Staphylococcus aureus*) | >128 | 16 | >8 |
| NRS100 (*Staphylococcus aureus*) | >128 | 8 | >16 |
| NRS123 (*Staphylococcus aureus*) | 32 | 4 | 8 |
| NRS384 (*Staphylococcus aureus*) | 16 | 2 | 8 |
| 10307570 (*Staphylococcus aureus*) | 16 | 2 | 8 |
| 11090306 (*Staphylococcus aureus*) | 2 | 1 | 2 |

TABLE 2

Minimum antibiotic concentrations needed for bactericidal (>3 $\log_{10}$)
activity on planktonic cultures of various bacterial species and strains
within 4-6 hours.

| Bacterial Strain | Antibiotics, (μg/ml) | | Fold reduction |
|---|---|---|---|
| | Penicillin | Penicillin + HL* | |
| D39 (*Streptococcus pneumoniae*) | >5,000 | 20 | >250 |
| SP670 (*Streptococcus pneumoniae*) | >5,000 | 20 | >250 |
| | Erythromycin | Erythromycin + HL* | |
| D39 (*Streptococcus pneumoniae*) | >1,000 | 200 | >5 |
| JY53 (*Streptococcus pneumoniae*) | >1000 | 200 | >5 |
| | Gentamicin | Gentamicin + HL* | |
| D39 (*Streptococcus pneumoniae*) | >500 | 50 | >10 |
| EF3030 (*Streptococcus pneumoniae*) | >500 | 50 | >10 |
| | Gentamicin | Gentamicin + HL** | |
| NRS384 (*Staphylococcus aureus*) | 50 | 5 | 10 |

TABLE 2-continued

Minimum antibiotic concentrations needed for bactericidal (>3 $log_{10}$) activity on planktonic cultures of various bacterial species and strains within 4-6 hours.

| Bacterial Strain | Antibiotics, (µg/ml) | | Fold reduction |
|---|---|---|---|
| | Methicillin | Methicillin + HL** | |
| NRS1 (*Staphylococcus aureus*) | >128 | 64 | >2 |
| NRS70 (*Staphylococcus aureus*) | 128 | 4 | 32 |
| NRS71 (*Staphylococcus aureus*) | >128 | 64 | >2 |
| NRS100 (*Staphylococcus aureus*) | >128 | 64 | >2 |
| NRS123 (*Staphylococcus aureus*) | >128 | 16 | >8 |
| NRS384 (*Staphylococcus aureus*) | >128 | 8 | >16 |
| 10307570 (*Staphylococcus aureus*) | >128 | 16 | >8 |
| 11090306 (*Staphylococcus aureus*) | 64 | 4 | >16 |

*50 µg/mL HL
**100 µg/mLHL

TABLE 3

Minimum antibiotic concentrations needed for bactericidal (>3 $log_{10}$) activity on biofilms formed by various bacterial species and strains within 4-6 hours for *S. pneumoniae* biofilms and 12 hours for *S. aureus* biofilms.

| Bacterial Strain | Antibiotics, (µg/ml) | | Fold reduction |
|---|---|---|---|
| | Penicillin | Penicillin + HL* | |
| D39 (*Streptococcus pneumoniae*) | >5000 | 100 | >50 |
| SP670 (*Streptococcus pneumoniae*) | >5000 | 100 | >50 |
| | Erythromycin | Erythromycin + HL* | |
| D39 (*Streptococcus pneumoniae*) | >1000 | 500 | >2 |
| JY53 (*Streptococcus pneumoniae*) | >1000 | 500 | >2 |
| | Gentamicin | Gentamicin + HL** | |
| D39 (*Streptococcus pneumoniae*) | >600 | 200 | >3 |
| EF3030 (*Streptococcus pneumoniae*) | >600 | 200 | >3 |
| | Methicillin | Methicillin + HL* | |
| NRS70 (*Staphylococcus aureus*) | >1000 | 250 | >4 |
| 11090306 (*Staphylococcus aureus*) | >1000 | 250 | >4 |

*250 µg/mL HL
**100 µg/mLHL

TABLE 4

Minimum antibiotic concentrations needed for bactericidal (>3 $log_{10}$) activity on murine nasopharyngeal colonization formed by various bacterial species and strains within 12 hours.

| Bacterial Strain | Antibiotics, (µg/dose) | | Fold reduction |
|---|---|---|---|
| | Penicillin | Penicillin + HL* | |
| SP670 (*Streptococcus pneumoniae*) | >100 | 10 | >10 |
| | Gentamicin | Gentamicin + HL* | |
| EF3030 (*Streptococcus pneumoniae*) | 100 | 3 | 33.3 |
| | Methicillin | Methicillin + HL** | |
| NRS70 (*Staphylococcus aureus*) | >100 | 10 | >10 |

*50 µg ALAFACT dose (single)
**100 µg ALAFACT dose (single)

Example 2

This example demonstrates that sublethal concentrations of ALAFAC potentiate the effect of common antibiotics (penicillins, macrolides, and aminoglycosides). Using MIC assays and short-time killing assays we observed that significantly reduced concentrations of antibiotics were needed to kill pneumococci. The antibiotic-resistant strains, could be brought into the clinically sensitive range by use of ALAFAC. Using a biofilm model in vitro and nasopharyngeal colonization in vivo, a combination of ALAFAC and antibiotics completely eradicated both biofilms and colonization in mice of both antibiotic-sensitive and resistant strains, something each agent alone was unable to do. While not intending to be bound by any particular theory, it is believed that ALAFAC-potentiation of antibiotics was partially due to increased accessibility of antibiotics to the bacteria, but relied more on calcium import and kinase activation. The sensitizing effect was not confined to species sensitive to ALAFAC. The ALAFAC-resistant respiratory species *Acinetobacter baumanii* and *Moraxella catarrhalis* were all sensitized to various classes of antibiotics in the presence of ALAFAC, activating the same mechanism as in pneumococci. Combined these results suggest the presence of a conserved ALAFAC-activated pathway that circumvents antibiotic resistance in bacteria. The ability to activate this pathway may extend the lifetime of the current treatment arsenal.

The ability of ALAFAC to potentiate the effect of the antibiotics was tested for three antibiotics—gentamicin, erythromycin and penicillin against both sensitive and resistant pneumococcal strains. An increased activity of combination therapy was observed on pneumococcal biofilms both in vitro and in a mouse model of nasopharyngeal colonization. The potentiating effect of ALAFAC was so strong that antibiotic-resistant strains grown in biofilms or colonizing the murine nasopharynx could be effectively eradicated in the presence of ALAFAC at concentrations effective against sensitive strains.

Materials and Methods. Reagents. Cell culture reagents, Bocillin FL and the Alexa Fluor 488 labeling kit were from Invitrogen, Carlsbad, Calif. Bacterial and cell culture media and reagents were from VWR Inc, Radnor, Pa. Chemically defined bacterial growth medium (CDM) was obtained from JRH Biosciences, Lexera, Kans. Sheep Blood was purchased from BioLink, Inc, Liverpool, N.Y. All antibiotics and remaining reagents were purchased from Sigma-Aldrich, St. Louis, Mo.

Production of ALAFAC. ALAFAC was produced by converting native alpha-lactalbumin in the presence of oleic acid (C18:1) as described. ALAFAC was generously provided by Dr. Catharina Svanborg. Lund University, Lund, Sweden.

Cells and Bacterial Strains. NCI-H292 bronchial carcinoma cells (ATCC CCL-1848) were grown on various surfaces as described. Pneumococcal strains were grown in a synthetic medium (CDM) or in Todd Hewitt medium containing 0.5% yeast extract (THY) as described. The study used the serotype 19F strain EF3030, the serotype 2 strain D39, its unencapsulated derivative AM1000, the D39 derivative lacking PspA through an insertion of an Erythromycin containing resistance cassette (JY53) and a clinical penicillin-resistant pneumococcal serotype 6 strain SP670. *Acinetobacter baumanii* and *Moraxella catarrhalis* strains were generously provided by Dr. Anthony Campagnari, University at Buffalo, SUNY. *A. baumanii* strains AB307 and AB979 and *M. catarrhalis* strains 7169 and BC8 were cultured in Mueller-Hinton (MH) medium at 37° C. with rotary shaking at 225 rpm and stored at −80° C. in 50% MH broth and 50% glycerol.

In vitro susceptibility tests. Minimal inhibitory concentrations (MICs) were determined in 96-well microtiter plates using the microdilution method according to approved standards of the CLSI except that Todd-Hewitt medium supplemented with 0.5% yeast extract, which yields reproducible MIC results was used as the test medium for *S. pneumoniae*. MICs for *A. baumanni*, and *M. catarrhalis* were determined in MH media. Two-fold dilutions of a starting antibiotic concentration was added in triplicate into microtiter plate wells (in 96-well plates), were seeded with a final bacterial concentration of $\sim 10^5$ colony forming units (CFU)/mL, and was incubated for 18 h in ambient air at 37° C. in a Synergy II microplate reader (Biotek, Winooski, Vt.) where the $OD_{600}$ was recorded every 5 minutes to monitor bacterial growth. The MIC was defined as the lowest concentration of antimicrobial agent solution at which no increase in $OD_{600}$ was detected.

Short-time kill assays. In late logarithmic growth phase, the bacteria were harvested by centrifugation at 12,000×g for 10 minutes and resuspended in phosphate-buffered saline (PBS; 30 mM $Na_2HPO_4$, 10 mM $KH_2PO_4$, 120 min NaCl, pH 7.4). Appropriate concentrations of the bacteria (around $10^8$ colony forming units per ml) were suspended in PBS and treated with indicated concentrations of ALAFAC and/or antibiotics for various times. The effect on bacterial viability was assessed by plating serial dilutions of bacterial sample on tryptic soy agar plates containing 5% sheep blood (viable counts) and determining viable CFUs after overnight growth at 37° C. A bactericidal activity was defined as a reduction of at least 3 $\log_{10}$ of the original inoculum.

Static Biofilm Model. Pneumococci were grown in CDM to mid-logarithmic phase ($OD_{600}=0.5$), washed, and resuspended in fresh pre-warmed medium to a density of $2\times10^4$ CFUs in 500 µl volume, and suspensions were used to seed sterile round glass coverslips in the bottom of polystyrene 24-well plates with a substratum of confluent H292 epithelial cells as described. Biofilms were cultured at 34° C. in 5% $CO_2$ for indicated times with change of culture media every 12 hours and used for SEM studies or to assess biomass and antibiotic resistance by viable plate counts.

To test antibiotic sensitivity of the biofilms, pre-formed biofilms were washed with PBS to eliminate planktonic bacteria and were exposed to PBS with indicated concentrations of ALAFAC and/or antibiotics for 3 hours at 34° C. in 5% $CO_2$. Biofilms were then washed in PBS, dispersed by sonication, and collected by pipetting in 100 µL PBS followed by a rinse with 100 µL PBS. Collected cells were then vortexed twice for 20 seconds at high speed and the dispersed biofilm cells were used to determine viable CFUs per ml from diluted samples plated and grown on blood agar. Results are reported as the total number of CFUs per biofilm.

ALAFAC potentiation of Gentamicin and Penicillin in vivo. Six-week-old female BALB/cByJ mice from Jackson Laboratories (Bar Harbor, Me., U.S.A.) were maintained in filter-top cages on standard laboratory chow and water ad libitum until use.

Mice were colonized as described. In short, 20 µl of a bacterial suspension containing $5\times10^6$ CFUs of EF3030 pneumococci in PBS or $1\times10^8$ CFUs of SP670 pneumococci in PBS were pipetted into the nares of non-anesthetized mice. After 48 hours, mice were treated with 20 µl gentamicin (0-5,000 µg/mL) or 20 µl penicillin (0-5,000 µg/mL) in the presence or absence of 100 µg (5,000 µg/mL) ALAFAC in the nares for 6 hours. Colonization burden was then assessed after euthanizing the animals by enumerating viable bacteria both in a nasopharyngeal lavage obtained by injecting 100 μL PBS in the trachea of mice and collecting it as it flowed out the nares, and from harvested nasopharyngeal tissue after the nasal wash. Nasopharyngeal tissue was dissected out as described by removing the upper skull bone, and harvesting the tissue present in the nasal conchae with forceps. Bacterial load was measured by determining viable plate counts from the nasal lavage or from homogenized tissue.

Scanning Electron Microscopy. Planktonic bacteria or biofilms grown in vitro (see above) were fixed using 2.5% glutaraldehyde, 0.075% ruthenium red and 0.075 M lysine acetate in 0.1 M sodium cacodylate buffer, pH 7.2 for 1 hr at room temperature. This procedure has been shown to retain carbohydrate structures and improve preservation of biofilm morphology. Samples were washed three times without shaking for 15 min at room temperature in 0.075% ruthenium red in 0.2 M sodium cacodylate buffer and were then dehydrated with a graded series of ethanol (10, 30, 50, 75, 95, and 100%) at room temperature with 15 min used for each step. Samples were exchanged into 100% hexamethyldisilazane, and allowed to air dry before being mounted onto stubs, carbon coated and analyzed using an SU70 Scanning Electron Microscope at an acceleration voltage of 5.0 kV available through the South Campus Instrumentation Center, University at Buffalo, N.Y.

Conjugation of Gentamicin with Alexa Fluor 488. Conjugation of gentamicin with Alexa Fluor 488 was performed using the Alexa Fluor 488-conjugation kit (Invitrogen), adapted from the manufacturer's instructions. Alexa Fluor 488 ester was added to a rapidly stirred solution of 0.1 M sodium bicarbonate, pH 8.3 and 10 mg/mL gentamicin and was incubated for 5 hr at 4° C. A gentamicin/Alexa Fluor molar ration of 10:1 was used to minimize formation of multiply substituted Alexa-Fluor 488-gentamicin conjugates. After conjugation, the conjugated gentamicin was separated from unreacted dye using a provided desalting resin. The concentration of the final product was estimated using the molar extinction coefficient of Alexa Fluor 488. 488-conjugated gentamicin was shown to retain its antimicrobial activity in the conjugated form and was stored at 4° C. until used.

Gentamicin and Bocillin FL Binding. We adapted a previously described method using Alexa Fluor 488-gentamicin, and Bocillin FL as reporter antibiotics to investigate association of these compounds with the pneumococcal cells. In brief, indicated strains were grown in THY medium to an optical density at 600 nm of 0.5. Antibiotics were added at the following concentrations: gentamicin at 50 μg/mL, Bocillin FL at 2 μg/mL, or a combination of gentamicin 50 μg/mL and ALAFAC 50 μg/mL, or Bocillin FL 2 μg/mL and ALAFAC 15 μg/mL.

After 30 minutes, cultures were centrifuged at 9000×g for 4 min, washed four times with PBS and ground with 0.2 μm glass beads for 15 min using a Mini bead beater (Biospec Products Inc). The cultures were then resuspended in a small volume of saline. The Bocillin FL or 488-gentamicin concentration was determined before and after grinding by measuring the amount of fluorescent material in a Synergy II microplate reader (Biotek, Winooski, Vt.) using excitation and emission wavelengths set at 485 and 530 nm, respectively. For Alexa Fluor 488-gentamicin, linearity was obtained between 2 and 800 μg/mL; ($R^2$=0.9983) with binding values expressed as a ratio of the sample protein content. For Bocillin FL, linearity was obtained between 0.5 and 100 μg/mL; ($R^2$=0.9928) with binding expressed as a ratio of the fluorescence of each sample divided with the sample protein content.

Statistical Analysis. The data in all were analyzed for statistical significance by a two-tailed Student's t-test for paired or unpaired data, as appropriate. A P-value <0.05, was considered significant.

Results. ALAFAC lowers the minimal inhibitory concentration of penicillin, erythromycin, and gentamicin, especially in resistant strains. We have earlier shown that pneumococci resistant to a several classes of antibiotics are equally sensitive to ALAFAC death, suggesting that ALAFAC uses a different mechanism of action than these agents. This was confirmed in this example as all strains included in the example, whether sensitive or resistant to antibiotics, had the same minimal inhibitory concentration (MIC) for ALAFAC. Based on the increasing use of combination therapy in infectious diseases, we were therefore interested in investigating the potential synergistic effects between ALAFAC and common antibiotics.

In the absence of ALAFAC, the MIC of the penicillin-compound penicillin G was 0.01 μg/ml for both the penicillin-sensitive strains S. pneumoniae strains D39 (serotype 2) and EF3030 (serotype 19F, from a child with otitis media) (Table 5). Simultaneous presence of subinhibitory concentrations of ALAFAC (15 μg/ml for this batch or 0.75× its MIC) reduced the MIC of penicillin G five-fold, to 0.002 μg/ml (FIG. 6A). To investigate whether the potentiation of ALAFAC held true also in pneumococcal strains resistant to penicillin G, the penicillin-resistant serotype 6A otitis media strain SP670 with an MIC of 4 μg/ml was tested in a similar way. In the presence of 0.75×MIC of ALAFAC, this strain became susceptible to penicillin showing a 20-fold decreased MIC of 0.2 μg/ml, that was significantly more decreased than the penicillin-sensitive strains (P<0.05; Table 5).

Importantly, ALAFAC-potentiation had the ability to place this strain in the penicillin-sensitive range, where penicillin would again be a potentially useful therapeutic agent.

The same pattern was true for the macrolide erythromycin. The addition of 0.75×MIC of ALAFAC, reduced the MIC of erythromycin for the sensitive strain D39 3-fold and the MIC of the erythromycin-resistant strain JY53, (carrying an erythromycin resistance cassette in the pspA locus) a dramatic 300-fold (P<0.001) to 0.01 μg/ml, making this strain highly susceptible to this antibiotic and equally sensitive as the non-resistant D39 strain in the presence of ALAFAC (Table 5).

Finally, the MIC of the aminoglycoside gentamicin, to which pneumococci show relative tolerance, was reduced 4-fold in the presence of 0.75×MIC of ALAFAC for both S. pneumoniae D39 and EF3030 (FIG. 6B and Table 5). Moreover, the addition of 17 μg/ml of ALAFAC (85% of the MIC) decreased the MIC of gentamicin for both strains 8-fold, indicating that a sub-inhibitory concentration of ALAFAC could sensitize S. pneumoniae to gentamicin in a concentration-dependent manner (Table 5). Combined these results suggest that ALAFAC potentiates the anti-pneumococcal effects of various classes of antibiotics with a significantly better potentiation occurring in antibiotic-resistant strains.

ALAFAC potentiates short-time pneumococcal kill by gentamicin, penicillin and erythromycin. To further verify the potentiation effect of ALAFAC for common antibiotics we performed short-time killing assays Similar to the MIC values, all strains, irrespective of antibiotic sensitivity, were equally sensitive to ALAFAC and required a concentration of approximately 15 times the MIC concentration to eradicate each inoculum in 1 hour, a further support that ALAFAC uses a different activation mechanism than the antibiotics used in this example.

Gentamicin at high concentrations reduced the inoculum 1.4 $\log_{10}$ after 1 hour of incubation, whereas both penicillin G and erythromycin lacked any bactericidal activity alone against the sensitive strains D39 and EF3030, even at concentrations as high as 5,000 µg/ml and 1,000 µg/ml, respectively, over that period of time. Treatment with these antibiotics was therefore performed over 4 hours. For each of these experiments, ALAFAC and each antibiotic were titrated to produce less than 1 $\log_{10}$ kill in sensitive strains, respectively, over the incubation time, and those concentrations were then used to perform combination treatments.

For penicillin G, a range of concentrations from 1 to 100 µg were tested, with the most successful combination effect seen using 50 µg/ml of ALAFAC and 20 µg/ml of penicillin G that alone caused no bactericidal activity (FIG. 7A). However, combination treatment of the two agents resulted in significantly higher killing than the added killing of each agent alone ($P<0.05$) with near eradication of the 7.5 $\log_{10}$ bacterial inoculum (FIG. 7A). To obtain a similar activity with ALAFAC alone, more that 5-fold higher concentrations were required, and penicillin failed to kill more than 2.6 $\log_{10}$ by itself, even at a 50-fold higher concentration (1,000 µg/ml) for 4 hours. The potentiation effect was also present in the penicillin-resistant strain SP670 that had a 20-fold higher MIC than the D39 strain, using the same concentrations of penicillin G and ALAFAC ($P<0.001$ compared to the additive killing effect of both agents alone; FIG. 7B). Increasing the penicillin concentration to 30 µg/mL (that had no bactericidal activity by itself) resulted in even more effective synergistic killing ($P<0.001$; FIG. 7B).

Similar and even stronger effects were seen when a sublethal concentration of ALAFAC was combined with erythromycin. As with penicillin G, a range of erythromycin concentrations (1-1,000 µg/ml) was tested and concentrations that produced no bactericidal activity alone but synergistic effects with ALAFAC were used. Combination of 50 µg/ml of ALAFAC and 200 µg/ml of erythromycin resulted in significantly increased killing than the added killing of each agent alone after 4 hours ($P<0.001$) with near-eradication of the inoculum (FIG. 7C). When using the erythromycin-resistant strain JY53 that displayed a 100-fold higher MIC, combination treatment with the two agents at the same concentrations was somewhat less effective but still caused a bactericidal activity significantly higher than the additive killing of each agent alone ($P<0.05$), which could be increased to complete eradication of the bacterial inoculum when 300 µg/ml erythromycin ($P<0.001$) was used together with 50 µg/mL ALAFAC, a highly significant synergy in killing of erythromycin-resistant pneumococci (FIG. 7D).

Finally, the effect of combination treatment with ALAFAC and gentamicin using 50 µg/ml of ALAFAC or 50 µg/ml of the aminoglycoside gentamicin induced bactericidal activity significantly enhanced compared with the additive killing of the two agents ($P<0.001$) with the entire bacterial inoculum eradicated after only 1 hour of incubation (FIG. 7E). This was substantial as gentamicin was unable to kill more than 1.4 $\log_{10}$ by itself, even at concentrations up to 1,000 µg/ml.

Combined these results suggest that ALAFAC acts as a powerful bactericidal potentiator producing synergistic effects with several classes of antibiotics and is able to significantly decrease the antibiotic concentrations needed to induce death of pneumococci.

ALAFAC/antibiotic combination treatment potentiate killing of in vitro biofilms. To address the role of ALAFAC's potentiating effect on antibiotic function under physiological conditions, we first subjected pneumococci growing as biofilms to combination treatment with ALAFAC and antibiotics. We and others have shown that pneumococci colonizing or infecting the mucosal surfaces of the host grows primarily in aggregated communities or biofilms that are well known to display substantially increased resistance to antibiotics as well as other antimicrobial agents.

Pneumococcal biofilms were formed with D39 pneumococci for 48 hours over a pre-fixed epithelial substratum. We used an epithelial substratum rather than an abiotic substratum as we have recently shown that biofilm growth on epithelial cell surfaces results in biofilms with higher biomass, higher antimicrobial resistance and more structural resemblance to biofilms observed during nasopharyngeal colonization in vivo than biofilms grown on abiotic surfaces. Various concentrations of ALAFAC and penicillin alone or in combination were tested to find the optimal synergy. When treating mature biofilms with 250 µg/ml of ALAFAC and 100 µg/ml of penicillin that by themselves were not bactericidal, as defined by at least 3 $\log_{10}$ death of the bacteria, the effect was significantly enhanced with 5.2 $\log_{10}$ pneumococci killed out of the 8.3 $\log_{10}$ total biofilm biomass, which was significantly higher than the additive effect of the two agents ($P<0.05$; FIG. 8A).

ALAFAC's anti-biofilm potentiation of was even more evident when the penicillin-resistant strain SP670 was used. Mature biofilms formed by this strain over a pre-fixed epithelial substratum showed almost complete resistance to treatment with either ALAFAC (250 µg/mL) or penicillin (100 µg/mL) alone. However the combination of ALAFAC and penicillin demonstrated a dramatic and synergistic bactericidal effect, significantly higher than the additive effect of the two agents ($P<0.01$; FIG. 8B).

Even more pronounced results were seen for erythromycin. D39 biofilms formed for 48 hours and treated with erythromycin alone (500 µg/ml) showed no bactericidal effects (FIG. 8C). In contrast, the combination of erythromycin with 250 µg/ml ALAFAC resulted in a synergistic increase in anti-biofilm activity with the near eradication of the biofilm biomass, which was significantly higher than the additive effect of both agents ($P<0.05$; FIG. 8C). The effect on the erythromycin-resistant strain JY53 was less pronounced with a more additive effect observed after treatment with 500 µg/mL erythromycin in combination with 250 µg/ml ALAFAC, which was not significantly different from the additive effect of each agent ($P=0.12$; FIG. 8D).

Finally, pneumococcal biofilms formed with EF3030 pneumococci for 48 hours were treated with 100 µg/mL ALAFAC and either 200 µg/ml or 500 µg/mL gentamicin alone or in combination for 3 hours. Neither concentration of gentamicin was bactericidal, whereas the combined treatment of the biofilms with both agents for 3 hours induced a bactericidal activity, which were both significantly higher than the additive effect of both agents ($P<0.05$ and $P<0.01$, respectively for 200 and 500 µg/ml gentamicin; FIGS. 8E and F). Scanning electron microscopy of EF3030 biofilms 3 hours after treatment with a combination of both ALAFAC and gentamicin also demonstrated a marked change in the appearance of the biofilm, with near eradication of all adherent bacteria from the epithelial cell substratum (FIG. 8J). In contrast, treatment with either agent alone yielded only minimal reductions in the density of adherent bacteria and matrix (FIGS. 8H and I) compared to untreated biofilms (FIG. 8G).

Increased eradication of nasopharyngeal colonization in mice using combined antibiotic-ALAFAC treatment. Pneumococci produce complex biofilms in the nasopharynx during asymptomatic colonization that are highly resistant to antimicrobial treatment. We therefore evaluated the ability of ALAFAC to potentiate the activity of traditional antibiotics in a murine colonization model in vivo.

Bacteria were inoculated intra-nasally for 48 hours with S. pneumoniae EF3030 and the established bacterial colonization was then treated once with increasing doses of gentamicin alone or in combination with 50 μg ALAFAC locally in the nares for 6 hours. The viability of bacteria both in a nasal wash and the nasopharyngeal tissue was measured by viable counts. Colonized mice treated with vehicle alone (phosphate-buffered saline) showed a colonization rate of $4\times10^6$ CFU per tissue with an approximate 10-fold lower presence of bacteria in the nasal wash ($7\times10^5$ CFU/ml). Mice treated with ALAFAC alone showed no decrease in bacterial burden either in the tissue or in the nasal lavage, whereas gentamicin alone caused a slow reduction of the bacterial burden starting at a dose of 3 μg/mouse in the nasal lavage and 10 μg/mouse in the nasopharyngeal tissues (FIGS. 9A and B).

However, mice treated with a combination of the two agents showed a significantly increased death of the bacteria removed by nasal lavage, compared with those treated with gentamicin alone (FIG. 9A). A statistically significant reduction of the bacterial burden in the presence of ALAFAC was evident already at a dose of 3 μg of gentamicin (150 μg/ml) whereas a 10-fold higher dose (1,500 μg/ml) was required to eradicate nasal lavage-associated bacteria with gentamicin alone. Bacteria associated with the tissue were highly resistant to gentamicin and substantial growth was detected even after a dose of 100 μg (5,000 μg/ml), 10 times the killing dose in the short time killing assay in vitro (FIG. 9B). However, in the presence of ALAFAC, a comparable decrease in tissue associated bacterial load was obtained using a 33-fold lower dose of gentamicin (3 μg; FIG. 9B).

Using the same procedure, mice we also colonized intra-nasally for 48 hours with the penicillin-resistant strain SP670 and then treated with increasing doses of penicillin alone or in combination with 50 μg ALAFAC locally in the nares, and bacterial viability in the nasal lavage and nasopharyngeal tissue was assessed after 12 hours. Untreated mice showed a colonization rate of $\sim1\times10^5$ CFU associated with each nasopharyngeal tissue with only around $2\times10^2$ CFUs present per 100 μl nasal wash. ALAFAC treatment alone resulted in no decrease in the pneumococcal burden. In mice treated with increasing does of penicillin alone both tissue-associated bacteria and lavage-associated bacteria were completely resistant to penicillin treatment up to an intranasal dose of 100 μg (5,000 μg/ml) (FIGS. 9C and D).

In contrast, in the presence of 50 μg of ALAFAC, near complete eradication of all lavage-associated bacteria was observed using 10 μg penicillin (P<0.05) and fewer than 10 colony forming units per lavage was detected at 100 μg penicillin, which was not statistically different from the effect of the 10 μg treatment (FIG. 9C). Similarly, a significant decrease (2 $\log_{10}$) in colonization of the nasopharyngeal tissue was seen already at 1 μg penicillin (50 μg/ml), a dose 100-fold lower than in mice treated with penicillin alone over the same treatment period, and at 100 μg/ml all the bacteria were eradicated in the presence of ALAFAC with no change in colonization observed with penicillin G alone (FIG. 9D).

These results support the fact that ALAFAC's potentiating effects on antibiotic activity functions under in vivo conditions and can potentiate the effect of antibiotics against strains resistant to the same antibiotic.

Effect of ALAFAC on gentamicin uptake and beta lactam binding to pneumococci. In a first attempt to address the mechanism of ALAFAC-potentiation of antibiotic activity, we evaluated the effect of sub-lethal ALAFAC-treatment on the binding/uptake or cell association of fluorescently labeled gentamicin and the beta-lactam Bocillin FL (a fluorogenic derivative of penicillin V). Bacterial cultures of sensitive D39 pneumococci were incubated with the reporter antibiotics in the presence or absence of subinhibitory concentrations of ALAFAC. After allowing the antibiotics to associate with the bacteria, they were washed and lysed by bead-beating, and the fluorescence of the lysate was determined and compared to a standard curve. The addition of 0.75×MIC of ALAFAC significantly increased the cell-associated level of gentamicin 2.58-fold (P<0.001; FIG. 10A).

In contrast, sublethal levels of ALAFAC had minimal impact on the binding of the beta-lactam Bocillin FL to sensitive D39 pneumococci. The addition of 15 μg/mL ALAFAC increased binding of Bocillin FL 1.07-fold compared with the bacteria treated with Bocillin FL alone, which was significantly higher, although not biologically relevant. A more dramatic increase in binding was seen to the penicillin-resistant strain SP670 where the addition of ALAFAC increased binding 1.75-fold compared with the Bocillin alone treated culture, however this was not statistically significant (FIG. 10B).

ALAFAC-induced sensitization of pneumococci to antibiotics requires calcium influx and kinase activation. As it was unlikely that increased antibiotic access was the only mode whereby ALAFAC potentiates the bactericidal activity of antibiotics, we further analyzed known ALAFAC effector functions. Calcium transport inhibition with ruthenium red, sodium/calcium exchange inhibition with amiloride and dichlorobenzamil (DCB), and kinase inhibition with staurosporine have all been shown to reduce the loss of membrane potential, reduce calcium influx in S. pneumoniae in response to ALAFAC at lethal concentrations and protect pneumococci from ALAFAC-induced death (FIG. 11A). To evaluate whether the same activation pathway was involved in ALAFAC-induced antibiotic sensitization in pneumococci, when non-lethal concentrations of ALAFAC were used, we performed a short time kill assay (1 hour incubation time) using gentamicin and ALAFAC or penicillin G and ALAFAC-combination treatment, in the presence of staurosporine (20 μM) or Ruthenium Red (30 μM). Both inhibitors completely abolished ALAFAC's antibiotic potentiation effect on both gentamicin and penicillin G (FIGS. 11B and C). These results suggest that the same pathway used when ALAFAC induces bactericidal activity alone play a critical role for ALAFAC's antibiotic potentiation effects.

ALAFAC-antibiotics combination therapy does not result in pneumococcal lysis. Most agents that kill pneumococci, including ALAFAC and cell wall-active anti-bacterials activate the major autolysin LytA to induce lysis of the bacteria, which can easily be detected by eye as a clearing of the bacterial suspension upon treatment and measured by a decrease in $OD_{600\ nm}$ over time. In comparison, antibiotics acting on bacterial DNA, RNA, or protein synthesis show reduced, though still significant, levels of cell lysis. However, during our combination treatments with ALAFAC and gentamicin above we observed no detectable lysis. To quantitate this phenomenon, autolysis of pneumococcal strain D39 was quantified in response to ALAFAC alone or a combination treatment with ALAFAC and Gentamicin (50 ng/mL each) using optical density. ALAFAC alone at a lethal concentration (250 µg/ml) produced a rapid lysis of the inoculum, whereas the combination of sublethal concentrations of ALAFAC and gentamicin, that induced equal level or death as the high concentration of ALAFAC alone, produced no change in $OD_{600}$ (FIG. 12A). Even a non-bactericidal concentration of ALAFAC (50 µg/ml) alone resulted in a small decrease in optical density at 600 nm ($OD_{600}$) whereas gentamicin at a low concentration failed to lyse the bacteria (FIG. 12A). Scanning electron microscopy of pneumococci after treatment with either agent alone or in combination confirmed that while ALAFAC-induced killing of S. pneumoniae results in autolysis of the bacterial cells, combination treatment with ALAFAC and another antibiotic did not result in lysis and only intact cells were observed (FIG. 12B). The lack of lysis from combination treatment may be beneficial for the host in reducing the host inflammation associated with bacterial components after lysis.

ALAFAC combination treatment is active also on species resistant to ALAFAC-induced death. During the studies of ALAFAC's bactericidal activity we observed that species resistant to ALAFAC respond to ALAFAC-treatment with depolarization of the bacterial membrane, but that this depolarization did not trigger bacterial death. Depolarization and ion transport is also observed in pneumococci treated with concentrations of ALAFAC that not trigger death. We were therefore interested in examining whether the membrane signaling induced in ALAFAC-resistant species could also potentiate antibiotic activity. Thus, we investigated the MIC values for two gram-negative respiratory pathogens, Moraxella catarrhalis and Acinetobacter baumanii, with high levels of inherent resistance to antibiotics.

Both M. catarrhalis strain 7169 and BC8 had MICs for ALAFAC that exceeded 750 µg/ml and MICs for penicillin that exceeded 50 µg/ml. In the presence of 50 µg/ml ALAFAC the MIC for penicillin was reduced over 32-fold to 1.56 µg/ml for strain 7169 and over 4-fold to 12.5 µg/mL for BC8 (Table 5). The MIC for gentamicin was 25 µg/ml in both strains. In the presence of 50 µg/ml of ALAFAC the reduction in gentamicin MIC in these strains was also significant, but less pronounced (about 4-fold; Table 5). Similarly, treatment of A. baumanii AB307 and AB979 that had MICs for ALAFAC that exceeded 1,000 µg/ml and MICs for penicillin that exceeded 100 µg/ml, the presence of 50 µg/ml of ALAFAC reduced the MIC of penicillin 4-fold for both strains (Table 5). The MICs for gentamicin was 36 µg/ml and 2.5 µg/ml for strains AB307 and AB979, respectively, which were lowered 8-fold and 2-fold respectively in the presence of 50 µg/ml of ALAFAC (Table 5). The potentiating effect of ALAFAC for all species against gentamicin was abolished in the presence of 30 µM RuR, suggesting that the same mechanism that is activated by ALAFAC in pneumococci is activated in other bacterial species.

Combined these results indicate that ALAFAC can potentiate the effects of antibiotics in strains that are resistant to ALAFAC's bactericidal effect and suggest that the initial depolarization and ion transport events important for both bacterial death and antibiotic potentiation in pneumococci is activated in other organisms.

TABLE 5

MIC determination of ALAFAC/antibiotic combination therapy.

| Bacterial Strain | MIC (µg/mL) | | | Fold reduction |
|---|---|---|---|---|
| | ALAFAC | Penicillin | Penicillin + HL | |
| S. pneumoniae D39 | 20 | 0.01 | 0.002* | 5 |
| S. pneumoniae EF3030 | 20 | 0.01 | 0.002* | 5 |
| S. pneumoniae SP670 | 20 | 4 | 0.2* | 20 |
| A. baumanii AB307 | >1,000 | >100 | 25*** | >4 |
| A. baumanii AB979 | >1,000 | >100 | 25*** | >4 |
| M. catarrhalis 7169 | >1,000 | >50 | 1.56*** | >32 |
| M. catarrhalis BC8 | 750 | >50 | 12.5*** | >4 |
| | ALAFAC | Erythromycin | Erythromycin + HL | |
| S. pneumoniae D39 | 20 | 0.03 | 0.01* | 3 |
| S. pneumoniae JY53 | 20 | 3 | 0.01* | 300 |
| | ALAFAC | Gentamicin | Gentamicin + HL | |
| S. pneumoniae D39 | 20 | 16 | 4* | 4* |
| S. pneumoniae D39 | 20 | 16 | 2** | 8** |
| S. pneumoniae EF3030 | 20 | 16 | 4* | 4* |
| S. pneumoniae EF3030 | 20 | 16 | 2** | 8** |
| A. baumanii AB307 | >1,000 | 36 | 4.5*** | 8 |
| A. baumanii AB979 | >1,000 | 2.5 | 1.25*** | 2 |
| M. catarrhalis 7169 | >1,000 | 25 | 6.7*** | 4 |
| M. catarrhalis BC8 | 750 | 25 | 6.7*** | 4 |

*HL (ALAFAC) used at a concentration of 0.75X MIC (15 µg/mL)
**HL (ALAFAC) used at a concentration of 0.85X MIC (17 µg/mL)
***ALAFAC used at a concentration of 50 µg/mL In this example we have shown that sublethal levels of HAMLET dramatically increase the efficacy of broad spectrum antibiotics, belonging to three different classes, against both pneumococci and HAMLET-resistant species, reducing their MIC and increasing short time killing activity, as well as increasing effects on biofilm growth and nasopharyngeal colonization, with highest efficacy against antibiotic-resistant strains.

The studies showed stronger potentiation effects of combination treatment than have been reported and also had the advantage that the time needed to obtain significant synergistic effects in time-kill assays were considerably shorter than those reported by others, with rapid synergism detected as early as 1 hour in the combination of HAMLET and gentamicin and within 4 hours for the combination of HAMLET and erythromycin or penicillin. By reducing the time required for pathogen inactivation, the possibility of establishing further infection is reduced.

Current estimates suggest that more than 65% of all human bacterial infections are the result of microbial growth as biofilms. Despite the availability of antimicrobial agents with excellent in vitro activity, the treatment of pneumococcal biofilm infections remains problematic. Pneumococcal biofilms have recently been implicated both in infection and colonization where they become 10 to 1000 times more resistant to antibiotics both in vitro and in vivo. The results therefore suggests that HAMLET has the potential to restore the effectiveness of β-lactam and macrolide antibiotics against resistant populations, extending their useful life and spectrum, as well as potentially decreasing the therapeutic dose of antibiotic-sensitive species that would result in less pressure for resistance spread in the population.

Combining a natural component of human milk that has already been used in mice, rats and humans as an anti-cancer therapy without showing any toxic side effects with traditional antibiotics, and thus targeting the bacteria simultaneously by separate mechanisms, synergistically produces antimicrobial activity that is greater than when each of the active compounds are used individually. This opens up the possibility to use HAMLET or HAMLET's activation pathway to potentiate antibiotic treatment and potentially treat antibiotic-resistant strains of various disease-causing species and extend the use of the current treatment arsenal.

Example 3

This example is another illustration of the potentiation ability of ALAFAC. In this example we demonstrate that ALAFAC acts as an antimicrobial adjuvant that can increase the activity of a broad spectrum of antibiotics (methicillin, vancomycin, gentamicin and erythromycin) against multi-drug resistant *Staphylococcus aureus*, such that they become sensitive to those same antibiotics, both in antimicrobial assays against planktonic and biofilm bacteria and in an in vivo model of nasopharyngeal colonization. While not intending to be bound by any particular theory, our results show that ALAFAC exerts these effects specifically by dissipating the proton gradient and inducing a sodium-dependent calcium influx that partially depolarizes the plasma membrane. These effects results in an increased cell associated binding and/or uptake of penicillin, gentamicin and vancomycin, especially in resistant strains. Finally, ALAFAC inhibits the increased resistance of methicillin seen under antibiotic pressure and the bacteria do not become resistant to the adjuvant, which is a major advantageous feature of the molecule. These results highlight ALAFAC as a novel antimicrobial adjuvant with the potential to increase the clinical usefulness of antibiotics against drug resistant strains of *S. aureus*.

In this example, we used a broad spectrum of antibiotics, including methicillin, erythromycin, gentamicin and vancomycin on multi-drug resistant *S. aureus* in vitro and in vivo. We also show that ALAFAC inhibits the development of clones with increased methicillin resistance when a MRSA population is exposed to increasing concentrations of the antibiotic and that the bacteria cannot overcome ALAFAC's inhibitory effect.

Materials and Methods. Reagents. Cell culture reagents, Bocillin FL and the AlexaFluor 488 labeling kit were from Invitrogen, Carlsbad, Calif. Bacterial and cell culture media, and supplies were from VWR Inc, Radnor, Pa. Sheep Blood was purchased from BioLink, Inc, Liverpool, N.Y. All antibiotics and remaining reagents were purchased from Sigma-Aldrich, St. Louis, Mo. Methicillin and gentamicin stocks were suspended in water while erythromycin and vancomycin stocks were dissolved in ethanol. Antibiotic stocks were diluted at least 100-fold in phosphate buffered saline (PBS), pH 7.4, before use in the assays.

Production of ALAFAC. ALAFAC was produced by converting EDTA-treated, partially unfolded alpha-lactalbumin in the presence of oleic acid (C18:1) on an anion-exchange matrix to a stable protein-lipid complex, as described and was resuspended in PBS for all experiments.

Bacterial Strains. Staphylococcal strains were grown in Tryptic Soy Broth (TSB) as described. The use of MRSA and VISA strains of *S. aureus* was approved by the Biosafety Committee at the University at Buffalo, SUNY. Network on Antimicrobial Resistance in *Staphylococcus aureus* (NARSA) strains NRS 1, 70, 71, 100, 123, 384 (all MRSA strains), the MRSA strain 10307570, and the MSSA strain 11090306 were generously provided to us by Dr. Alan Lesse, University at Buffalo, SUNY.

In vitro susceptibility tests. Minimal inhibitory concentrations (MICs) were determined in 96-well microtiter plates using the microdilution method according to approved standards of the CLSI as described previously. However, rather than Mueller-Hinton broth, Tryptic soy broth (TSB) was used for susceptibility testing as it is the common media used for Staphylococcal growth, and as it has shown more consistent results for a variety of antimicrobials when tested against Staphylococci. This was true also for ALAFAC as when traditional Mueller Hinton broth was used, approximately 20% more ALAFAC was required for equivalent adjuvant activity as seen in TSB. A two-fold dilution series of antibiotics in triplicate and in the presence or absence of ALAFAC was prepared in 96 well microtiter plates, and each well was seeded with a final bacterial concentration of $10^5$ CFU/mL, and was incubated for 24 h at 37° C. in a Synergy 2 microplate reader (Biotek, Winooski, Vt.) where the Optical Density at 600 nm ($OD_{600}$) was recorded every 5 minutes to monitor bacterial growth. The MIC was defined as the lowest concentration of antimicrobial agent solution where no increase in $OD_{600}$ was detected. For MIC assays involving ion inhibitors, Ruthenium Red (RuR; 30 µM) or Amiloride (1 mM), were used along with a concentration of methicillin (4 µg/mL or 10 µM) that only completely inhibited growth in combination with ALAFAC (100 µg/mL or 6 µM).

Minimal bactericidal concentrations (MBCs) were determined as described from the MIC assay plates, by plating 10 µL of broth from all wells without visible growth as well as from the wells with the highest concentration of antimicrobials that still showed visible growth onto sheep blood agar plates. The MBC was defined as the lowest concentration of antimicrobials yielding colony counts <0.1% (3 $\log_{10}$ reduction) of the initial inoculum (as determined by colony counts from the growth control well immediately after inoculation) as described.

Static Biofilm Model. Staphylococci were grown in TSB to mid-logarithmic phase ($OD_{600}$=0.5), washed, and resuspended in fresh pre-warmed medium to a density of 2×10$^4$ CFU in 500 µl volume, and suspensions were used to seed polystyrene 24-well plates. Bacteria were cultured at 37° C. for 12 hours, after which biofilms were washed with PBS to eliminate planktonic bacteria and were exposed to TSB with indicated concentrations of ALAFAC and/or antibiotics for 24 hours at 37° C. Biofilms were then washed in PBS, sonicated and detached by scraping the surface in the presence of 100 µL PBS followed by a rinse with 100 µL PBS. Collected cells were vortexed twice for 20 seconds at high speed and the dispersed biofilm cells were first observed by microscopy to ensure proper dispersion and then diluted in a 10-fold dilution series where 100 µl of each dilution was plated on blood agar plates to determine viable CFUs per ml after overnight growth at 37° C. Colony counts from plates carrying 20-200 colonies were used to determine the viable counts and are reported as the total number of colony-forming units per biofilm.

ALAFAC potentiation of Gentamicin and Penicillin in vivo. Six-week-old female BALB/cByJ mice from Jackson Laboratories (Bar Harbor, Me., U.S.A.) were maintained in filter-top cages on standard laboratory chow and water ad libitum until use.

Mice were colonized as described. In short, 10 µl of a bacterial suspension containing 5×10$^7$ CFUs of NRS 70 staphylococci in PBS were pipetted into the nares of non-anesthetized mice. After 24 hours, mice were treated with 20 µl methicillin (0-100 µg or 0-5,000 µg/mL) in the presence or absence of 20 µl (100 µg) ALAFAC in the nares for 12 hours. Colonization burden was then assessed after euthanizing the animals by enumerating viable bacteria both in a nasopharyngeal lavage obtained by injecting 100 µL PBS in the trachea of mice and collecting it as it flowed out the nares, and from harvested nasopharyngeal tissue after the nasal wash. Nasopharyngeal tissue was dissected out as described by removing the upper skull bone, and harvesting the tissue present in the nasal conchae with forceps. Bacterial load was measured by determining viable plate counts from the nasal lavage or from homogenized tissue as described above.

Assessing membrane potential. Staphylococci grown to late log phase in TSB were pelleted by centrifugation at 2,400×g for 10 minutes and washed twice by resuspension in PBS. The bacterial pellet was resuspended in PBS to half of the original volume and energized with 50 mM glucose for 15 minutes at 37° C. To measure membrane potential of the staphylococcal membrane, 500 nM $DiBAC_4(3)$ (bis-(1, 3-dibutylbarbituric acid) trimethine oxonol; Molecular Probes, Eugene, Oreg., USA) were added. In a 96-well plate, a 100 µL volume of this bacterial suspension was then added to 100 µL of PBS containing vehicle alone or ALAFAC and antibiotic combinations in the presence or absence of specific ion transport inhibitory compounds yielding a final concentration of 25 mM glucose and 250 nM $DiBAC_4(3)$ per well. Triton X-100 (0.1%; Sigma-Aldrich) was used as a positive control for membrane depolarization and rupture. The plate was then placed immediately into a pre-warmed (37° C.) Synergy 2 Multi-Mode Microplate Reader (BioTek) where fluorescence readings from $DiBAC_4(3)$ (485/20 nm excitation, 528/20 nm emission) were taken every minute for one hour. The difference in fluorescence intensity between the untreated control and the ALAFAC-treated sample was calculated for the "no inhibitor" samples and for the "inhibitor" samples using the values after 60 minutes. The fluorescence intensity difference for the "inhibitor" samples was then expressed as fold change of the intensity compared with the ALAFAC alone ("no inhibitor") sample, providing the degree of depolarization compared to the "ALAFAC alone" sample.

Radioisotope $^{45}Ca^{2+}$ transport assays. Staphylococcus aureus was grown to log phase, washed three times and resuspended in 1×PBS containing 0.5 mM $CaCl_2$ (CaPBS). No glucose was added in order to minimize the interference created by extrusion of $Ca^{2+}$ via ATPase pumps. $^{45}CaCl_2$ (PerkinElmer; Waltham, Mass., USA) was added to the cells at a final concentration of 2.5 µCi/mL, followed by inhibitor compound, with each addition given two minutes equilibration time. The untreated baseline sample was measured at this point. The sample was then divided, ALAFAC was added to one of the tubes, and $^{45}Ca^{2+}$ uptake was measured at various intervals. For each sample, 100 µL was dispensed onto Millipore 0.3 µm PHWP filters (EMD Millipore; Billerica, Mass., USA) presoaked in CaPBS, and immediately washed with 9 mL of CaPBS via syringe filtration through Millipore Swinnex® filter holders. Filters were placed in scintillation vials with 5 mL of scintillation fluid, and CPMs were detected on a Wallac 1409 liquid scintillation counter (Wallac Oy, Turku, Finland). The results were expressed as ΔCPM that was calculated for each sample at the indicated time points as the difference between ALAFAC-treated and untreated samples.

Intracellular pH measurement. A reported protocol for intracellular pH ($pH_i$) measurement was modified and optimized for S. aureus by testing the effect of various dye concentrations and staining times on the measured fluorescence of S. aureus isolate NRS 384 grown to mid-log phase. Cell samples were subjected to increasing concentrations of the membrane-permeant acetoxymehtyl (AM) ester derivative of the dual-excitation ratiometric pH indicator dye BCECF (2',7'-bis-(2-carboxyethyl)-5-(and-6)-carboxyfluorescein), for 30 minutes at 30° C. Fluorescence was measured as a ratio of fluorescence at 530 nm with dual wavelength excitation at 490 and 440 nm and calibration curves were established for each independent experiment. After testing a number of loading concentrations we observed that the fluorescence ratios remains generally constant when concentrations above 20 µM was used. Therefore 25 µM BCECF-AM was used for all experiments. The optimized staining time, 30 minutes, was determined using the same criteria and was used for all experiments. After loading, the cells were washed twice in PBS by centrifugation and the resulting pellet was resuspended in PBS to the original volume and ALAFAC and ALAFAC/antibiotic combinations were added. CCCP was added as a positive control. CCCP is a lipophilic weak acid that is soluble in the lipid domain of the membrane in both the protonated and deprotonated form. This allows it to act as a protonophore causing an influx of $H^+$ into the cytoplasm, dissipating both the electrical potential and the $H^+$ gradient across the inner membrane. For each experiment calibration was performed where cells were resuspended in high [$K^+$] buffers at different pH values ranging from 6.5 to 8.0. Nigericin (20 µM; a potassium/hydrogen antiport with some ionophore activity for both ions) and valinomycin (20 µM; a potassium ionophore) were added in combination to the samples to equilibrate the $pH_i$ of the cells to the pH of the surrounding buffer as described both for the creation of a standard curve during calibration, and at the end of each experiment to demonstrate the pH of the experimental buffer.

Membrane Integrity Assays. To evaluate the effect of ALAFAC on membrane integrity, Staphylococci were exposed to ALAFAC and antibacterial agents at indicated concentrations for 50 minutes at 37° C. in PBS. The detergent Triton X-100 (0.1%) was used as a control, known to cause extensive membrane rupture. After treatment the leakage of soluble components (DNA RNA and protein) were measured from supernatant obtained after centrifugation of the bacterial suspension at 13,000×g for 5 min, by measuring the absorbance at 260 nm in a BioTek Synergy 2 plate reader with the Take3 microdrop addition (Biotek). Cellular release of the small molecule ATP (MW 507) that was measured from the same supernatants using the ATP determining kit (Invitrogen), which measures the luminescence of oxyluciferin produced from the oxidation of luciferin by luficerase, a process that requires ATP degradation. The uptake of the membrane impermeable DNA binding dye propidium iodide (MW 668) was measured by the fluorescence intensity of the whole bacterial suspension after 50 min in a Synergy 2 Microplate Reader (BioTek; 528/20 nm excitation, 605/20 nm emission). Where applicable, independent readings were also taken in the presence of antibacterial agents alone to enable corrections for potential background leakage.

Conjugation of Gentamicin with Alexa Fluor 488. Conjugation of gentamicin with AlexaFluor 488 was performed using the AlexaFluor 488-conjugation kit (Invitrogen), adapted from the manufacturer's instructions as described. In short, AlexaFluor 488 ester was added to a rapidly stirred solution of 0.1 M sodium bicarbonate, pH 8.3 and 10 mg/mL gentamicin, and was incubated for 5 hours at 4° C. A gentamicin/AlexaFluor molar ratio of 10:1 was used to minimize formation of multiply substituted Alexa-Fluor 488-gentamicin conjugates. Conjugated gentamicin was separated from unreacted dye using a provided desalting resin. Conjugation efficiency was determined by measuring the moles of dye per mole gentamicin. The absorbance of the conjugated antibiotic was determined at 494 nm and divided by 71,000 $M^{-1}$ $cm^{-1}$, the molar extinction coefficient for AlexaFluor 488 at 494 nm, and the concentration of gentamicin in the sample (estimated based on a minimum retention of 80% after purification over the resin). The conjugation efficiency was 1.2 moles AlexaFluor 488 per mole gentamicin in the batch used. The conjugated gentamicin was shown to retain its anti-microbial activity and was stored at 4° C. until used.

Gentamicin, Vancomycin and Bocillin FL Binding. We adapted a previously described method using AlexaFluor 488-gentamicin, vancomycin FL and Bocillin FL as reporter antibiotics to investigate association of these compounds with the staphylococcal cells. In brief, indicated strains were grown in TSB to an $OD_{600nm}$ of 0.5. Antibiotics were added at the following concentrations: Gentamicin at 50 µg/mL, Vancomycin FL at 20 µg/mL, Bocillin FL at 25 µg/mL alone, or in combination with ALAFAC at 100 µg/mL.

After 30 minutes, cultures were centrifuged at 9,000×g for 4 min, washed four times with PBS, and resuspended in a small volume of PBS. Cells were lysed by 5 successive freeze thaw cycles at −80° C. and 37° C. for 5 min each as described. The Bocillin FL, vancomycin FL or Alexa Fluor 488-gentamicin concentration was determined by measuring the amount of fluorescent material in a Synergy 2 microplate reader (Biotek) using excitation and emission wavelengths set at 485 and 530 nm, respectively. Linearity was obtained between 2 and 800 µg/mL; ($R^2$=0.9983) for AlexaFluor 488-gentamicin, between 0.5 and 100 µg/mL; ($R^2$=0.9928) for Bocillin FL, and between 0.25 and 50 µg/mL; ($R^2$=0.9919) for Vancomycin FL, with binding expressed as a ratio of the fluorescence of each sample divided with the sample protein content, determined by the 280/260 nm ratio using the using a BioTek Synergy 2 plate reader with the Take3 microdrop addition (Biotek)

ALAFAC and Methicillin Resistance Development. Experiments were designed to test the impact of ALAFAC on the adaptation of MRSA to methicillin in liquid cultures, and to test ALAFAC's potential to inhibit resistance increase during antibiotic pressure. Series of tubes containing two-fold increasing concentrations of methicillin (1-512 µg/ml or 2.5-1,350 µM) in the absence or presence of ALAFAC (100 µg/ml or 6 µM) were incubated with MRSA (NRS 384; $10^7$-$10^8$ cfu/ml innocula), as described for MIC determination above. After 12 hours of incubation, 0.1 mL samples from the tubes containing the highest antibiotic concentration that still showed turbidity were used to inoculate a new series of tubes containing the same antibiotic serial dilution series in the presence and absence of ALAFAC. The experiments were performed over 10 cycles. After each cycle and additional 0.1 mL bacteria from the tubes with the highest antibiotic concentration that still showed turbidity were washed twice in PBS to eliminate the antibiotics and ALAFAC. These bacteria were then used to determine their MIC in the absence or presence of 6 µM ALAFAC in a separate assay, as described above. These assays provided the MIC values for FIG. 18, and helped us evaluate the effect of ALAFAC on adaptation to methicillin and the response of these bacteria to ALAFAC's adjuvant activity Statistical Analysis. The data were analyzed for statistical significance by a two-tailed Student's t-test for unpaired data. A P-value <0.05, was considered significant.

Results. Sensitizing activity of ALAFAC on antibiotics in vitro. A standard checkerboard broth microdilution assay was used to test whether ALAFAC interfered with the susceptibility of bacteria to antibiotics that target cell wall synthesis (methicillin and vancomycin) as well antibiotics that target protein synthesis (erythromycin and gentamicin). ALAFAC alone had no activity against any of the S. aureus strains tested even at concentrations exceeding 5,000 µg/ml. However, in the presence of ALAFAC-concentrations as low as 100 µg/mL (6 µM), all S. aureus strains tested showed 2 to >16 fold reductions in the minimal concentration that inhibited growth (MIC) of methicillin (FIG. 13, Table 6), vancomycin, erythromycin and gentamicin (Table 6) and 2 to >32 fold reductions in the minimal bactericidal concentration (MBC) of these same antibiotics (Table 6). Some of the MIC and MBC-reductions may well be larger as the assay did not go beyond 128 and 256 µg/ml, respectively, at which concentration several strains still grew normally. The addition of 6 µM ALAFAC in the assays decreased the MIC for methicillin more in resistant strains compared with the methicillin-sensitive strains of S. aureus (MSSA). Furthermore, for both MRSA and MSSA strains, the fold decrease in the MBC concentrations in the presence of ALAFAC was generally more pronounced than the decrease in the MIC concentrations (Table 6). This was also observed when ALAFAC was added in combination with other antibiotics, with the exception of gentamicin that showed a more pronounced reduction in MIC in the presence of ALAFAC with less of an effect on the MBC (Table 6).

Although 6 µM of ALAFAC could make three of the strains sensitive to methicillin and gentamicin (Table 6) this concentration was insufficient to make the remaining strains sensitive. However, using increased concentrations of ALA- FAC (requiring at most 54 µM), all antibiotic-resistant strains could be converted to methicillin, gentamicin, erythromycin and vancomycin sensitivity (Table 6, Last column).

Similar to the MIC and MBC assays, treatment of bacteria grown to mid-log phase (approximately $10^8$ CFU/ml) with antibiotics alone or in combination with ALAFAC resulted in the same phenotype with immediate bacteriostatic effects followed by bactericidal activity after 6 hours of incubation at lower concentrations of antibiotics when ALAFAC was present. Combined these results suggest that ALAFAC potentiates the anti-staphylococcal effects of various classes of antibiotics with a significantly better potentiation seen in antibiotic-resistant strains (Table 6).

ALAFAC potentiates methicillin and vancomycin killing of in vitro biofilms. To address the role of ALAFAC's effect on antibiotic function under more physiological conditions, we first investigated the potentiating effects of ALAFAC on antibiotic activity against S. aureus biofilms. S. aureus biofilms were formed with the MRSA strain NRS 70 and the MSSA strain 11090306 overnight on polystyrene plates. As bacterial biofilms, including staphylococcal biofilms, are inherently resistant to most antimicrobials, higher concentrations of each agent were required to see bactericidal effects. Using either 200 µg/mL (12 µM) of ALAFAC or 250 µg/mL (660 µM) of methicillin alone failed to induce bactericidal activity over a 24-hour period (FIG. 14A), whereas a bactericidal effect (>3 $\log_{10}$ reduction in the number of viable bacteria) was observed against both the MRSA and the MSSA biofilms when the agents were combined (FIG. 14A).

ALAFAC was less active when used in combination with vancomycin against biofilms formed by the vancomycin-insensitive S. aureus (VISA) strain NRS 1 or the vancomycin-sensitive S. aureus (VSSA) strain NRS 384. Biofilms formed by these strains showed almost complete insensitivity to treatment with 32 µg/mL (21 µM) vancomycin alone, similar to published data, however the combination of ALAFAC and vancomycin demonstrated an increased death of staphylococcal biofilm bacteria over 24 hours that was significant for NRS 1 (P<0.05), but not for NRS 384 (FIG. 14B).

Finally, we tested the effect of gentamicin in combination with ALAFAC against the gentamicin resistant strains NRS 1 and the gentamicin-sensitive strains NRS 384. Neither ALAFAC (500 µg/ml; 30 µM) nor gentamicin (50 µg/ml; 105 µM) had any effect on the viability of either strain alone but in combination they produced significantly increased loss of bacterial viability (P<0.05 for both strains; FIG. 14C).

Reduction of nasal MRSA colonization by ALAFAC and methicillin in vivo. To determine the efficacy of ALAFAC/antibiotic combination treatment against MRSA colonization in vivo, mice were colonized with MRSA NRS 70 for 24 h and treated with one dose of either buffer (PBS) or methicillin in the presence or absence of ALAFAC (FIG. 15). Even administration of 100 µg of methicillin failed to significantly reduce the bacterial burden associated with the nasal mucosa compared with the buffer-alone treated control group. In contrast, administration of similar a amount of methicillin in combination with 100 µg ALAFAC caused a significant decrease in MRSA colonization in the nasopharyngeal tissue (P<0.05). This effect was also detected when a lower dose of methicillin (10 µg) was tested in the presence of 100 µg of ALAFAC (P<0.05).

ALAFAC adjuvant activity requires sodium dependent calcium influx. ALAFAC's bactericidal activity on pneumococci is associated with a sodium-dependent calcium influx that that is also induced in a range of bacterial species, including Staphylococci, where this influx does not result in death activation. We therefore hypothesized that this ion transport mechanism could play a role in ALAFAC-induced sensitization in S. aureus.

We first performed an MIC assay in the presence of the calcium transport inhibitor Ruthenium Red (RuR) and the sodium transport inhibitor Amiloride that reduces the calcium influx and loss of membrane potential in S. pneumoniae in response to ALAFAC, We found that the addition of either inhibitor completely abolished ALAFAC's antibiotic potentiation effect on Staphylococci (FIG. 16A), as well as the membrane depolarization associated with ALAFAC-potentiation (FIG. 16B). To confirm that the ALAFAC-induced membrane depolarization was associated with $Ca^{2+}$ transport we directly monitored uptake of $Ca^{2+}$ using the radioisotope $^{45}Ca^{2+}$. Intracellular $Ca^{2+}$ rose immediately upon ALAFAC addition, and was almost completely blocked in RuR treated cells (FIG. 16C).

This effect was unrelated to any effects on membrane integrity, as ALAFAC caused no membrane damage, indicated by a lack of propidium iodide staining of bacterial DNA inside the cells, or of leakage of ATP, DNA, or RNA into the culture supernatant (measured by a luciferase assay, or the absorbance of the supernatant at 260 nm, respectively, as described in the Materials section; data not shown). This was not surprising as ALAFAC is unable to kill S. aureus even at concentrations 50-fold higher than those used in these assays. These results suggest that ALAFAC-induced sensitization of S. aureus requires sodium-dependent calcium influx resulting in rapid depolarization of the transmembrane electrical potential of the staphylococcal membrane and is not associated with membrane disruption (FIG. 16C).

ALAFAC induces dissipation of the proton motive force. The observed effect of ALAFAC on membrane potential prompted us to examine other aspects of membrane function associated with antibiotic resistance. The proton motive force is composed of both the transmembrane electrical potential measured above, and the transmembrane chemical proton gradient both of which are important for drug efflux. To assess the effect of ALAFAC on the transmembrane proton gradient we measured the intracellular pH of cells after exposure to ALAFAC. A representative experiment is shown in FIG. 16D. As a positive control the hydrogen-ionophore CCCP was added ($1^{st}$ arrow—blue line). Addition of ALAFAC ($1^{st}$ arrow—red line) similarly resulted in rapid intracellular acidification and dissipation of the pH gradient. Preincubation of cells with Ruthenium red (purple line) or Amiloride (green line) did not fully inhibit ALAFAC-induced dissipation of the pH gradient ($1^{st}$ arrow), indicating that sodium-dependent calcium transport and dissipation of the proton gradient may be partially parallel or sequential. At the end of each experiment ($2^{nd}$ arrow) the pH gradient was completely dissipated using a combination of nigericin and valinomycin to induce a $pH_i$ of the external buffer (complete dissipation of the proton motive force). The results show that ALAFAC effectively dissipated the proton gradient.

ALAFAC increases gentamicin, vancomycin, and beta lactam association with staphylococcal cells. As ALAFAC dissipated the proton motive force, which is tightly associated with multidrug efflux pump function, we evaluated the effect of ALAFAC-treatment on the binding/uptake of fluorescently labeled gentamicin, vancomycin and the beta-lactam Bocillin FL (a fluorogenic derivative of penicillin V). In keeping with the results of the MIC assays we found that the addition of 100 µg/mL ALAFAC resulted in no significant increase in Bocillin FL association with the methicillin-sensitive strain, whereas ALAFAC-addition to the methicillin-resistant strain NRS 384 caused a significantly increased Bocillin FL-association compared with the Bocillin FL alone treated culture (P<0.01; FIG. 17A).

Similarly, the addition of ALAFAC did not increase the cell-associated levels of vancomycin in the vancomycin-sensitive strain but significantly increased the association with the VISA strain NRS 1 (P<0.01; FIG. 17B). The addition of ALAFAC also increased the cell-associated level of gentamicin 2.6 fold in the NRS384 strain, although not to a significant degree (data not shown, P=0.09). Combined these results suggest that ALAFAC's effect on membrane function resulted in an increased association of antibiotics with the bacterial cells particularly for resistant strains.

ALAFAC suppresses methicillin-resistance development in *S. aureus*, and *S. aureus* does not develop resistance to ALAFAC adjuvant activity. Antibiotic resistance is induced and enhanced with repeated exposure to increasing concentration of antibiotics, which may well have implications during clinical treatment. Thus, reducing resistance development upon repeated exposure would confer significant clinical benefits. To evaluate ALAFAC's potential effect on resistance development, experiments were designed to test the impact of ALAFAC on the resistance-development of MRSA to methicillin in liquid cultures.

For NRS 384 cultures grown in the absence of ALAFAC, the MIC of methicillin increased from 16 µg/ml to 512 µg/mL after 8 cycles of sequential incubation with increasing concentrations of methicillin (FIG. 18—blue line). Surprisingly, the addition of a low concentration of ALAFAC (100 µg/mL; 6 µM) drastically reduced this increased methicillin-resistance of the strain. After 10 cycles this culture had a methicillin MIC of only 64 µg/mL (FIG. 18—hatched blue line). When ALAFAC was present during the MIC testing, the highest concentration of methicillin that the strain was able to grow in was 8 µg/ml, the same fold reduction (8-fold) as observed before exposing the strain to cycles of increasing antibiotic concentrations, demonstrating that no resistance to ALAFAC's adjuvant activity occurred even after continuous incubation in 100 µg/mL ALAFAC for more than 10 cycles (FIG. 18—green hatched line). This suggests both that ALAFAC inhibits increased methicillin-resistance upon methicillin exposure and that *S. aureus* is unable to develop resistance to ALAFAC's adjuvant activity.

These studies demonstrate that even though ALAFAC showed no antimicrobial activity against any of the *S. aureus* strains used, ALAFAC acted as an effective antimicrobial adjuvant with the ability to increase the efficacy of a broad range of commonly used antibiotics including methicillin, vancomycin, erythromycin, and gentamicin, such that drug-resistant *S. aureus* could again become sensitive to these antibiotics both in in vitro. Similarly, we showed that the mechanism of ALAFAC-induced potentiation of various antibiotics was similar between *S. pneumoniae* and *S. aureus*. This shows that ALAFAC has the ability to act as an adjuvant to potentiate the activity of antibiotics irrespective of its ability to be bactericidal, and therefore, can act as an adjuvant on a wide range of bacterial species, including species with widespread multi-drug resistance where treatment options are rapidly becoming limited.

Treatment of MRSA infections depends on the clinical situation, the administration route, and the resistance pattern of the organism, but normally entails the use of drugs such as vancomycin, linezolid, daptomycin, clindamycin, and mupirocin. In vitro testing has shown some synergy in time-kill assays between daptomycin and oxacillin and a slight increase in eradication of MRSA biofilms with vancomycin in the presence of rifampicin and tigecycline. Additionally, non-bactericidal inhibitors of efflux pumps have been tested in *S. aureus* for their ability to lower MICs of antibiotics with some success. Although the daptomycin/oxacillin synergy was comparable to the potentiation effect of ALAFAC on methicillin, ALAFAC has a much stronger potentiation effect in eradicating biofilms, even at relatively low concentrations (6-30 µM, which amounts to 100-500 µg/mL as ALAFAC is a protein complex. These concentrations are well within the physiological range found in human milk (2,000 µg/mL)). In vivo treatment is primarily based on the use of vancomycin with linezolid and clindamycin as main adjunctive therapies and daptomycin is the antibiotic of choice in cases of vancomycin insensitivity, but both in vitro assays and in vivo treatment show that antibiotic combination treatment of MRSA invariably result in increased resistance of the agents used, producing increasingly multi-drug resistant strains, which continuously escalate the problems with MRSA treatment.

The adjuvant activity of ALAFAC presented in this study has at least three benefits in this regard. First, we could significantly decrease nasopharyngeal colonization with MRSA with just one administration of methicillin in the presence of ALAFAC for 12 hours. A topical decolonization model was chosen both based on the difficulty achieving decolonization clinically to prevent infection, as MRSA is a major cause of mucosal infections, and as ALAFAC is a non-covalently associated protein-lipid complex that is less effective when administered systemically, where serum proteins compete for binding of the lipid component. Methicillin was used for the studies mainly to verify that ALAFAC can reverse the resistance of this agent, that together with penicillins was safely employed topically early in its investigative history. Unfortunately, since then the rapid emergence of methicillin-resistant staphylococci has almost completely negated this value and practice and other antibiotics such as erythromycin or gentamicin that were once widely used topically have met a similar fate. Thus, the results show that ALAFAC can make methicillin and maybe other, currently unusable, antibiotics useful for treatment of mucosal surfaces and have the potential to offer a return to these safer agents for topical use.

Second, part of the mechanism for the increased adaptation of MRSA to ever-increasing levels of oxacillin with parallel increases of resistance to erythromycin, kanamycin, rifampicin and other antibiotics was recently shown to be associated with activation of efflux pumps that are sensitive to agents that dissipate the proton motive force, such as CCCP. CCCP is known to lower the MIC of fluoroquinolones, tetracyclines and other antibiotics due to its inactivation of efflux pumps that is driven by the proton motive force, but CCCP is so toxic that no molecules belonging to this family of energy-inhibitors has been developed for clinical use. ALAFAC have a major advantage in this regard, as it dissipates the proton motive force as effectively as CCCP but shows no toxicity to healthy human cells or to the *S. aureus* cells, indicating that ALAFAC's effect is more targeted and useful for drug development. It also has a major advantage as it does not directly interfere with efflux pump function as other potential adjuvants do, but causes both a rapid and sustained dissipation of the trans-membrane proton gradient and an influx of calcium through a sodium-dependent mechanism that induces dissipation of the electrical gradient without killing the organism, both of which were required for ALAFAC's potentiation effect. This dual membrane effect alters membrane ion gradients required for the activity of efflux pumps, as well as other resistance mechanisms that may explain ALAFAC's ability to reverse the resistance of a broad range of antibiotics in a broad range of species besides *S. aureus*. Thus ALAFAC may also affect target site alterations, enzymatic inactivation of antibiotic compounds, activity of beta-lactams on penicillin-binding proteins, and indirectly ATP production required for ATP-binding cassette-type multidrug transporters to pump drugs out of the cell, all of which are sensitive to the chemical environment of the cellular membrane. The ALAFAC-induced changes of the chemical membrane environment was therefore, not surprisingly, accompanied by an increase in the bacterial association of gentamicin, vancomycin and the beta-lactam Bocillin FL, with resistant strains accumulating more antibiotics. This suggests that ALAFAC-induced disruption of the proton motive force and ion gradients also acts by increasing antimicrobial penetration and binding.

The third benefit of ALAFAC's dual and potentially parallel actions on the bacterial membrane function is its ability to inhibit MRSA resistance-development after exposure to increasing methicillin concentrations. The presence of ALAFAC during methicillin-pressure significantly decreased the resistance development of the MRSA strain used. Additionally and importantly, even after continuous growth in ALAFAC, *S. aureus* did not become insensitive to ALAFACs adjuvant properties. Instead the strain that was continually grown in ALAFAC plus methicillin over many cycles showed both less resistance-increase to methicillin, and that the strain could still be equally sensitized in the presence of ALAFAC. This suggests that ALAFAC is not susceptible to the development of resistance and have the potential to reduce the emergence of multi-resistant mutants associated with increased efflux pump function or other resistance mechanisms. These results agree with findings in *S. pneumoniae* where tests of spontaneous mutation frequency have demonstrated that strains are unable to develop resistance to ALAFAC (7).

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A composition suitable for administration to an individual comprising:
    a) isolated alpha-lactalbumin fatty acid complex (ALAFAC), wherein the fatty acid in the complex comprises cis, unsaturated, C14, C16, C18 and/or C20 fatty acids; and
    b) an antibiotic,
in a pharmaceutical carrier, wherein a) is present at a concentration that potentiates the action of the antibiotic for treatment of an infection in the individual, but does not exhibit an antibacterial effect.

2. The composition of claim 1, wherein the fatty acids comprise oleic acid and/or linoleic acid.

3. The composition of claim 1, wherein alpha-lactalbumin in the complex is human.

4. The composition of claim 1, wherein the composition is in the form of a liquid, gel, paste, solid, semi-solid, or aerosolized form.

5. A method of treating a bacterial infection in an individual in need thereof comprising administering the composition of claim 1 via a topical or a mucosal route to the individual.

6. The method of claim 5, wherein the fatty acids comprise oleic acid and/or linoleic acid.

7. The method of claim 5, wherein the alpha-lactalbumin is human alpha-lactalbumin.

TABLE 6

MIC and MBC values for *S. aureus* strains exposed to various antibiotics in the absence and presence of ALAFAC

| Bacterial Strain | Antibiotics, MIC (μg/ml) | | MIC Fold reduction | Antibiotics, MBC (μg/ml) | | MBC Fold reduction | [HL]** to sensitize, μM |
|---|---|---|---|---|---|---|---|
| | Meth | Meth + HL* | | Meth | Meth + HL* | | |
| NRS1 | >128 | 16 | >8 | >256 | 64 | >4 | 48 |
| NRS70 | 32 | 1 | 32 | 128 | 4 | 32 | 3 |
| NRS71 | >128 | 16 | >8 | >256 | 64 | >4 | 54 |
| NRS100 | >128 | 8 | >16 | >256 | 64 | >4 | 18 |
| NRS123 | 32 | 4 | 8 | >256 | 16 | >16 | 12 |
| NRS384 | 16 | 2 | 8 | >256 | 8 | >32 | 6 |
| 10307570 | 16 | 2 | 8 | >256 | 16 | >16 | 6 |
| 11090306 | 2 | 1 | 2 | 64 | 4 | 16 | 0 |
| | Erm | Erm + HL* | | Erm | Erm + HL* | | |
| NRS384 | 16 | 4 | 4 | >256 | 16 | >16 | 6 |
| NRS123 | 0.5 | 0.25 | 2 | 16 | 4 | 4 | 0 |
| | Gent | Gent + HL* | | Gent | Gent + HL* | | |
| NRS384 | 1 | 0.00625 | 160 | 16 | 4 | 4 | 0 |
| NRS1 | >128 | 8 | >16 | >256 | 32 | >8 | 48 |
| | Vanc | Vanc + HL* | | Vanc | Vanc + HL* | | |
| NRS384 | 1 | 0.5 | 2 | 16 | 8 | 2 | 0 |
| NRS1 | 8 | 4 | 2 | 32 | 8 | 4 | 18 |

*HL = ALAFAC.
Concentration used was 100 μg/ml (6 μM)
**The last column describes the concentration of ALAFAC required to make each strain sensitive to the respective antibiotic.

8. The method of claim 5, wherein the bacterial infection is due to *Streptococcus pneumoniae, Staphylococcus aureus, Acenitobacter baumanii, Moraxella catarrhalis*, and/or *Haemophilus influenza*.

9. The method of claim 8, wherein the infection has become resistant to the antibiotic alone.

10. The method of claim 9, wherein the infection is due to MRSA.

11. A kit for treatment of bacterial infections comprising the composition of claim 1 and instructions for administration via a topical or a mucosal route to an individual in need thereof.

12. The kit of claim 11, wherein the antibiotic is selected from the group consisting of beta-lactam antibiotics, lipopeptides, protein synthesis inhibitors, DNA synthesis inhibitors, RNA synthesis inhibitors, mycolic acid synthesis inhibitors, and folic acid synthesis inhibitors.

13. The kit of claim 11, wherein the antibiotic is a Penicillin or a glycopeptide.

14. The kit of claim 11, wherein the composition is present in a lyophilized form and the kit further comprises a sterile liquid container for dispersion of said composition.

15. The kit of claim 11, wherein the formulation of a) is formulated for delivery via dermal or mucosal route.

16. The kit of claim 11, wherein the alpha-lactalbumin is human and the fatty acids comprise oleic acid.

* * * * *

UNITED STATES PATENT AND TRADEMARK OFFICE
CERTIFICATE OF CORRECTION

| | |
|---|---|
| PATENT NO. | : 9,526,766 B2 |
| APPLICATION NO. | : 14/412104 |
| DATED | : December 27, 2016 |
| INVENTOR(S) | : Hakansson et al. |

Page 1 of 1

It is certified that error appears in the above-identified patent and that said Letters Patent is hereby corrected as shown below:

In the Claims

Column 49, Line 33, in Claim 15, "formulation of a)" should read:
--composition--.

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*